US009212351B2

(12) United States Patent
Li et al.

(10) Patent No.: US 9,212,351 B2
(45) Date of Patent: Dec. 15, 2015

(54) RICE AND PRODUCTS THEREOF HAVING STARCH WITH AN INCREASED PROPORTION OF AMYLOSE

(75) Inventors: Zhongyi Li, Kaleen (AU); Matthew Kennedy Morell, Aranda (AU); Sadegur Rahman, Nicholls (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 474 days.

(21) Appl. No.: 13/462,629

(22) Filed: May 2, 2012

(65) Prior Publication Data

US 2012/0266267 A1 Oct. 18, 2012

Related U.S. Application Data

(60) Continuation of application No. 12/806,167, filed on Aug. 6, 2010, now Pat. No. 8,188,336, which is a division of application No. 10/577,564, filed as application No. PCT/AU2004/001517 on Oct. 27, 2004, now Pat. No. 7,790,955.

(60) Provisional application No. 60/515,102, filed on Oct. 27, 2003.

(51) Int. Cl.
| C12N 9/24 | (2006.01) |
| A23L 1/0522 | (2006.01) |
| C12N 9/10 | (2006.01) |
| A23L 1/10 | (2006.01) |
| A23L 1/182 | (2006.01) |
| C12N 15/82 | (2006.01) |

(52) U.S. Cl.
CPC .............. *C12N 9/107* (2013.01); *A23L 1/0522* (2013.01); *A23L 1/1041* (2013.01); *A23L 1/182* (2013.01); *C12N 15/8245* (2013.01); *A23V 2002/00* (2013.01)

(58) Field of Classification Search
CPC ...... C08B 30/042; C08B 30/00; C12N 15/00; C12N 2015/60
See application file for complete search history.

(56) References Cited

U.S. PATENT DOCUMENTS

| 3,690,896 | A | 9/1972 | Tarasewitz at al. |
| 4,770,710 | A | 9/1988 | Friedman et al. |
| 5,051,271 | A | 9/1991 | Iyengar et al. |
| 5,792,920 | A | 8/1998 | Bridges et al. |
| 6,013,861 | A | 1/2000 | Bird et al. |
| 6,083,547 | A | 7/2000 | Katta et al. |
| 6,107,060 | A | 8/2000 | Keeling et al. |
| 6,303,174 | B1 | 10/2001 | McNaught et al. |
| 6,307,125 | B1 | 10/2001 | Block et al. |
| 6,376,749 | B1 | 4/2002 | Broglie et al. |
| 6,392,120 | B1 | 5/2002 | Broglie et al. |
| 6,483,009 | B1 | 11/2002 | Poulsen et al. |
| 6,730,825 | B1 | 5/2004 | Goldsbrough et al. |
| 6,734,339 | B2 | 5/2004 | Block et al. |
| 6,897,354 | B1 | 5/2005 | Yamamori et al. |
| 6,903,255 | B2 | 6/2005 | Yamamori et al. |
| 6,916,976 | B1 | 7/2005 | Li et al. |
| 7,001,771 | B1 | 2/2006 | Morell et al. |
| 7,009,092 | B1 | 3/2006 | Jane et al. |
| 7,041,484 | B1 | 5/2006 | Baga et al. |
| 7,521,593 | B2 | 4/2009 | Regina et al. |
| 7,667,114 | B2 | 2/2010 | Morell et al. |
| 7,700,139 | B2 | 4/2010 | Bird et al. |
| 7,700,826 | B2 | 4/2010 | Morell et al. |
| 7,790,955 | B2 | 9/2010 | Li et al. |
| 7,812,221 | B2 | 10/2010 | Regina et al. |
| 7,888,499 | B2 | 2/2011 | Morell et al. |
| 7,919,132 | B2 | 4/2011 | Regina et al. |
| 7,993,686 | B2 | 8/2011 | Bird et al. |
| 8,115,087 | B2 | 2/2012 | Regina et al. |
| 8,178,759 | B2 | 5/2012 | Morell et al. |
| 8,188,336 | B2 | 5/2012 | Li et al. |
| 8,501,262 | B2 | 8/2013 | Bird et al. |
| 2003/0035857 | A1 | 2/2003 | Sroka et al. |
| 2004/0060083 | A1 | 3/2004 | Regina et al. |
| 2004/0199942 | A1 | 10/2004 | Morell et al. |
| 2004/0204579 | A1 | 10/2004 | Block et al. |
| 2005/0071896 | A1 | 3/2005 | Regina et al. |
| 2005/0164178 | A1 | 7/2005 | Morell et al. |
| 2006/0010517 | A1 | 1/2006 | Li et al. |
| 2006/0035379 | A1 | 2/2006 | Morell et al. |
| 2006/0204597 | A1 | 9/2006 | Bird et al. |

(Continued)

FOREIGN PATENT DOCUMENTS

| EP | 1692289 A0 | 12/2006 |
| GB | 2 360 521 | 9/2001 |

(Continued)

OTHER PUBLICATIONS

Supplemental Amendment in Response to Jul. 23, 2009 Office Action filed in connection with U.S. Appl. No. 10/577,564, filed Apr. 27, 2006.

Amendment in Response to Jul. 23, 2009 Office Action filed in connection with U.S. Appl. No. 10/577,564, filed Apr. 27, 2006.

Response to Restriction Requirement filed Dec. 12, 2008 in connection with U.S. Appl. No. 10/577,564.

Non-Final Office Action issued Feb. 19, 2009 in connection with U.S. Appl. No. 10/577,564.

Response to Non-Final Office Action filed Mar. 19, 2009 in connection with U.S. Appl. No. 10/577,564.

(Continued)

*Primary Examiner* — Brent T Page
(74) *Attorney, Agent, or Firm* — John P. White; Gary J. Gershik; Cooper & Dunham LLP

(57) ABSTRACT

Rice having reduced levels of starch branching enzymes produce grain having a high relative amylose content in the endosperm. The rice grain of this invention can be of a non-shrunken phenotype despite a lesion in the amylopectin synthesis pathway and may be transgenic or nontransgenic.

13 Claims, 11 Drawing Sheets

(56) References Cited

U.S. PATENT DOCUMENTS

| | | |
|---|---|---|
| 2006/0286186 A1 | 12/2006 | Bird et al. |
| 2007/0300319 A1 | 12/2007 | Li et al. |
| 2009/0226592 A1 | 9/2009 | Regina et al. |
| 2010/0330253 A1 | 12/2010 | Morell et al. |
| 2011/0010807 A1 | 1/2011 | Morell et al. |
| 2011/0045127 A1 | 2/2011 | Ral et al. |
| 2011/0059225 A1 | 3/2011 | Li et al. |
| 2011/0070352 A1 | 3/2011 | Regina et al. |
| 2011/0212916 A1 | 9/2011 | Bird et al. |
| 2011/0281818 A1 | 11/2011 | Jenkins et al. |
| 2012/0074247 A1 | 3/2012 | Regina et al. |
| 2012/0114770 A1 | 5/2012 | Regina et al. |
| 2012/0129805 A1 | 5/2012 | Li et al. |
| 2013/0115362 A1 | 5/2013 | Regina et al. |
| 2013/0156924 A1 | 6/2013 | Morell et al. |
| 2014/0044826 A1 | 2/2014 | Regina et al. |

FOREIGN PATENT DOCUMENTS

| | | |
|---|---|---|
| JP | 2007511207 | 10/2007 |
| KN | 10-2007-0001057 | 1/2007 |
| WO | WO 97/22703 | 6/1997 |
| WO | WO 99/66050 | 12/1999 |
| WO | WO 00/15810 | 3/2000 |
| WO | WO 00/66745 | 9/2000 |
| WO | WO 01/32886 | 5/2001 |
| WO | WO 01/062934 | 8/2001 |
| WO | WO 02/37955 | 5/2002 |
| WO | WO 02/010105 | 12/2002 |
| WO | WO 03/023024 | 3/2003 |
| WO | WO 03/094600 | 11/2003 |
| WO | WO 2005/001098 | 1/2005 |
| WO | WO 2005/040381 | 6/2005 |
| WO | WO 2006/069422 | 7/2006 |
| WO | WO 2011/011833 | 2/2011 |
| WO | WO 2012/053730 | 5/2012 |
| WO | WO 2012/103594 | 8/2012 |

OTHER PUBLICATIONS

Official Action, issued Sep. 22, 2008, in connection with U.S. Appl. No. 10/577,564.
Official Action, issued Jul. 23, 2009, in connection with U.S. Appl. No. 10/577,564.
Notice of Allowance and Fee(s) Due, issued Apr. 2, 2010, in connection with U.S. Appl. No. 10/577,564.
Official Action, issued Jul. 29, 2008, in connection with European Patent Application No. 04789648.5.
Amendment in Response to Jul. 29, 2008 Official Action, issued in connection with European Patent Application No. 04789648.5, filed Feb. 9, 2009.
Official Action, issued Sep. 2, 2009, in connection with European Patent Application No. 04789648.5.
Response to Official Action filed Mar. 12, 2010 in connection with European Patent Application No. 04789648.5.
Summons to Attend Oral Proceedings issued Oct. 22, 2010 in connection with European Patent Application No. 04789648.5.
Reply to Summons to Attend Oral Proceedings filed Mar. 11, 2011 in connection with European Patent Application No. 04789648.5.
Findings Upon Submissions Relating to Oral Proceedings, issued Apr. 21, 2011 in connection with European Patent Application No. 04789648.5.
Response to Official Action filed Jun. 29, 2011 in connection with European Patent Application No. 04789648.5.
Intention to Grant issued Aug. 10, 2011 in connection with European Patent Application No. 04789648.5.
Apr. 24, 2009 Examination Report issued in connection with Australian Patent Application No. AU2004284112.
May 21, 2010 Response to Examination Report filed in connection with Australian Patent Application No. AU2004284112.
Jun. 21, 2010 Response to Examination Report filed in connection with Australian Patent Application No. AU2004284112.
Jun. 25, 2010 Notice of Acceptance issued in connection with Australian Patent Application No. AU2004284112.
Official Action, issued Apr. 29, 2009, in connection with Australian Patent Application Publication No. AU2004284112.
Jul. 4, 2008 First Office Action issued in connection with Chinese Patent Application No. 2004800315896 (Chinese Language).
Jul. 4, 2008 First Office Action issued in connection with Chinese Patent Application No. 2004800315896 (English Language).
Nov. 18, 2008 Response to Office Action filed in connection with Chinese Patent Application No. 2004800315896 (Chinese Language).
Dec. 18, 2009 Second Office Action issued in connection with Chinese Patent Application No. 2004800315896 (Chinese Language).
Apr. 27, 2010 Third Office Action issued in connection with Chinese Patent Application No. 2004800315896.
May 10, 2010 English Language Translation of Apr. 27 2010 Third Office Action issued in connection with Chinese Patent Application No. 2004800315896.
Mar. 1, 2010 Response to Office Action filed in connection with Chinese Patent Application No. 2004800315896 (Chinese Language).
Sep. 15, 2010 Notice of Decision to Grant issued in connection with Chinese Patent Application No. 2004800315896 (Chinese Language).
Nov. 15, 2010 Examination Report issued in connection with Indian Patent Application No. 2132/DELNP/2006 (English Language).
Jan. 28, 2011 Response to First Examination Report filed in connection with Japanese Patent Application No. 2006-537005 (Japanese Language).
Nov. 8, 2011 Second Office Action issued in connection with Japanese Patent Application No. 2006-537005 (English Language).
Official Action, issued Feb. 25, 2009, in connection with Philippine Patent Application Publication No. 1-2006-500918.
Amendment in Response to Feb. 25, 2009 Official Action, issued in connection with Philippine Patent Application Publication No. 1-2006-500918, filed Jun. 23, 2009.
Feb. 25, 2009 Office Action issued in connection with Philippines Patent Application No. 1-2006-500918.
Jun. 23, 2009 Response to Office Action filed in connection with Philippines Patent Application No. 1-2006-500918.
Jan. 27, 2011 Office Action issued in connection with Philippines Patent Application No. 1-2006-500918.
Apr. 18, 2011 First Office Action issued in connection with Korean Patent Application No. 10-2006-7008107 (Korean Language).
Aug. 16, 2011 Arguments in Response to First Office Action filed in connection with Korean Patent Application No. 10-2006-7008107 (Korean Language).
Aug. 16, 2011 Amendment in Response to First Office Action filed in connection with Korean Patent Application No. 10-2006-7008107 (Korean Language).
Itoh et al., Introduction of Wx Transgene into Rice wx Mutants Leads to Both High- and Low-Amylose Rice. Plant Cell Physiol, 2003, 44(5):473-480.
James et al., Starch synthesis in the cereal endosperm. Current Opinion in Plant Biology, 2003, 6:215-222.
Kamijima et al., Relationships Between Kernel Weight and Occurrence of White-Core in Kernel of Rice. Sci. Rept. Fac. Agr. Kobe. Univ., 1984, 16:19-25.
Mizuno et al., Alteration of the Structural Properties of Starch Components by the Lack of an Isoform of Starch Branching Enzyme in Rice Seeds. The Journal of Biological Chemistry, 1993, 268(25)19084-19091.
Nakamura Y, Towards a Better Understanding of the Metabolic System for Amylopectin Biosynthesis in Plants: Rice Endosperm as a Model Tissue. Plant Cell Physiol, 2002, 43(7):718-725.
Swanston et al., Combining high-amylose and waxy starch mutations in barley. Journal of the Science of Food and Agriculture, 2001, 81:594-603.
File History of U.S. Pat. No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).

(56) References Cited

OTHER PUBLICATIONS

File History of U.S. Pat. No. 7,700,139, Bird et al., issued Apr. 20, 2010 (U.S. Appl. No. 11/324,063, filed Dec. 30, 2005).
File History of U.S. Patent Application Publication No. 2006-0286186, Bird et al., published Dec. 21, 2006 (U.S. Appl. No. 11/417,330, filed May 2, 2006).
File History of U.S. Patent Application Publication No. US 2011-0212916, Bird et al., published Sep. 1, 2011 (U.S. Appl. No. 12/799,013, filed Apr. 16, 2010).
File History of U.S. Pat. No. 7,790,955, Li et al., issued Sep. 7, 2010 (U.S. Appl. No. 10/577,564, filed Apr. 27, 2006).
File History of U.S. Pat. No. 7,888,499, Morell et al., issued Feb. 15, 2011 (U.S. Appl. No. 10/416,439, filed Dec. 5, 2003).
File History of U.S. Pat. No. 7,001,771, Morell et al., issued Feb. 21, 2006 (U.S. Appl. No. 10/018,418, filed May 9, 2002).
File History of U.S. Pat. No. 7,700,826, Morell et al., issued Apr. 20, 2010 (U.S. Appl. No. 11/231,599, filed Sep. 21, 2005).
File History of U.S. Pat. No. 7,521,593, Regina et al., issued Apr. 21, 2009 (U.S. Appl. No. 10/434,893, filed May 9, 2003).
File History of U.S. Pat. No. 7,919,132, Regina et al., issued Apr. 5, 2011 (U.S. Appl. No. 12/384,823, filed Apr. 9, 2009).
File History of U.S. Pat. No. 7,667,114, Morell et al., issued Feb. 23, 2010 (U.S. Appl. No. 10/204,347, filed Feb. 20, 2002).
File History of U.S. Patent Application Publication No. 2011-0010807, Morell et al., published Jan. 13, 2011 (U.S. Appl. No. 12/707,437, filed Feb. 17, 2010).
Jul. 7, 2011 Office Action, issued in connection with U.S. Appl. No. 12/806,167.
Oct. 7, 2011 Amendment in Response to Office Action, filed in connection with U.S. Appl. No. 12/806,167.
Dec. 15, 2011 Notice of Allowance, issued in connection with U.S. Appl. No. 12/806,167.
Abel, G.J.W. et al., "Cloning and functional analysis of a cDNA encoding a novel 139 kDa Starch Synthase from Potato (solanum tuberosum L.)," Plant J. 10(6): 981-991 (1996).
Ainsworth, C. et al., "Expression, organization and structure of the genes encoding the waxy protein (granule-bound starch synthase) in wheat," Plant Mol. Biol. 22:67-82 (1993).
Baba, T. et al., "Identification, cDNA cloning and gene expression of soluble starch synthase in rice (oryza stativa L.) Immature Seeds," Plant Physiol. 103:565-573 (1993).
Banks et al., "Studies on Starches of High Amylose Content," Starch 26: 289-300 (1974).
Batey and Curtin, "Measurement of Amylose/Amylopectin Ratio by High-Performance Liquid Chromatography," Starch 48: 338-344(1996).
Blauth et al., "Identification of Mutator Insertional Mutants of Starch -Branching Enzyme 2a in Corn," Plant Physiology 125:1396-1405 (2001).
Boyer and Preiss, "Evidence for Independent Genetic Control of the Multiple Forms of Maize Endosperm Branching Enzymes and Starch Synthases," Plant Physiology 67: 1141-1145 (1981).
Buleon et al., "Starch Granules: Structure and Biosynthesis," International Journal of Biological Macromolecules 23: 85-112 (1998).
Craig et al., "Mutations in the Gene Encoding Starch Synthase II Profoundly Alter Amylopectin Structure in Pea Embryos," The Plant Cell 10:413-426.
Denyer, K. et al., "Identification of Multiple Isoforms of Soluble and Granule Bound Starch Synthase in Developing Wheat Endosperm," Planta 196: 256-265 (1995).
Dry, I. et al., "Characterization of cDNAs encoding two isoforms of granule-bound synthase which show differential expression in developing storage organs of pea and potato," Plant J. 2(2): 193-202 (1992).
Edwards et al., "Biochemical and Molecular Characterization of a Novel Starch Synthase from Potato Tubers," Plant J. 8(2): 283-294 (1995).
Flipse et al., "Introduction of Sense and Antisense cDNA for Branching Enzyme in the Amylose-Free Potato Mutant Leads to Physico-Chemical Changes in the Starch," Planta 198: 340-347.

Fujita et al., "Grain and Starch Characteristics of the Double Recessive Lines for Amylose-free and High Amylose Gene in Barley," Breeding Science 49: 217-219 (1999).
Gao et al., "Triticum aestivum mRNA for Starch Synthase IIa-2 (wSs2a-2." EMBL Abstract Accession No. AJ269503, Jul. 6, 2000.
Gao et al., "Characterization of dull 1, a Maize Gene Coding for a Novel Starch Synthase," Plant Cell 10:399-412 (1998).
Gao and Chibbar, "Isolation, Characterization, and Expression Analysis of Starch Synthase IIa cDNA from wheat (Triticum aestivum L.)," Genome 43:768-775 (2000).
Goering and DeHass, "A Comparison of the Properties of Large- and Small-Granule Starch Isolated from Several Isogenic Lines of Barley," Cereal Chemistry 51:573-578 (1974).
Harn et al., "Isolation and Characterization of the zSSIIA and zSSIIb Starch Synthase cDNA Clones from Maize Engdosperm," Plant Mol. Biol. 37:639-649 (1998).
Holmes et al., Henderson's Dictionary of Biological Terms, 9th Ed., Van Nostrand Reinhold Co., New York, 1979, p. 218.
Klosgen, et al., "Molecular Analysis of the Waxy Locus of Zea mays," Mol. Gen. Genet. 203: 237-244 (1986.
Knight, et al., "Molecular Cloning of Starch Synthase I from Maize (w64) Endosperm and Expression in Escherichia coli," Plant J. 14(5): 613-622 (1998).
Kull et al., "Genetic Engineering of Potato Starch Composition: Inhibition of Amylose Biosynthesis in Tubers From Transgenic Potato Lines by the Expression of Antisense Sequences of the Gene for Granule-bound Starch Synthase," J. Genet. Breed. 49: 69-76 (1995).
Jansson et al., "Cloning, Characterization and Modification of Genes Encoding Starch Branching Enzymers in Barley." Starch: Structure and Functionality. Royal Society of Chemistry, London, pp. 196-203 (1997).
Jarvi and Eslick, "Shrunken Endosperm Mutants in Barley," Crop Science 15:363-366 (1975).
Li et al., "Triticum aestivum Starch Synthase IIa mRNA, Complete cds," EMBL Abstract Accession No. AF155217, Sept 7, 1999.
Li et al., "The Localization and Expression of the Class II Starch Synthases of Wheat," Plant Physiology 120:1147-1155.
Li et al., "Cloning and Characterization of a Gene Encoding Wheat Starch Synthase I," Theor. Appl. Genet. 98: 1208-1216.
Mazzolini et al., "Assaying synthetic ribozymes in plants: high-level expression of a functional hammerhead structure fails to inhibit target gene activity in transiently transformed protoplasts," Plant Mol. Biol. 20: 715-731 (1992).
Miao et al., "Evaluation and Characterization of an Endosperm-Specific sbella Promoter in Wheat," Chinese Science Bulletin 49(6): 579-585 (2004.
Mizuno et al., "Alteration of the Structural Properties of Starch Components by the Lack of an Isoform of Starch Branching Enzyme in Rice Seeds," J. Biol. Chem. 268(25): 19084-19091 (1993).
Morell et al., "The Biochemistry and Molecular Biology of Starch Synthesis in Cereals," Aust. J. Plant. Physiol. 22: 647-660 (1995).
Morell et al., "Barley sex6 Mutants Lack Starch Synthase iia Activity and Contain a Starch with Novel Properties," The Plant Journal 34:173-185 (2003).
Myers et al., "Recent Progress toward Understanding Biosynthesis of the Amylopection Crystal," Plant Physiology 122: 989-997 (2000).
Nakamura Y. (2002) Towards a Better Understanding of the Metabolic System for Amylopectin Biosynthesis in Plants: Rice Endosperm as a Model Tissue. *Plant Cell Physiol*. 43(7) : 718-725.
Nishi et al., "Biochemical and Genetic Analysis of the Effects of Amylose-Extender Mutation in Rice Endosperm." Plant Physiology 127:459-472 (2001).
Okagaki R.J., "Nucleotide Sequence of a Long cDNA from the Rice Waxy Gene," Plant Molecular Biology 19: 513-516 (1992).
Puchta, "Gene Replacement by Homologous Recombination in Plants," Plant Mol. Biol. 48: 173-182 (2002).
Rahman, Sadequr et al., "Comparison of Starch-Branching Enzyme Genes Reveals Evolutionary Relationships Among Isoforms. Characterization of a Gene for Starch-Branching Enzyme IIa from the Wheat D Genome Donor Aegilops tauschii," Plant Physiology 125: 1314-1324 (2001).

(56) References Cited

OTHER PUBLICATIONS

Rahman, S. et al., "A Complex Arrangement of Genes at a Starch Branching Enzyme I Locus in the D-genome Donor of Wheat," Genome 40: 465-474 (1997).
Rahman, S. et al., "The Major Proteins of Wheat Endosperm Starch Granules," Aust. J. Plant Physiol., 22:793-803 (1995).
Rahman, S. et al., "Characterisation of a Gene Encoding Wheat Endosperm Starch Branching Enzyme-I," Theor. Appl. Genet. 98: 156-163 (1999).
Safford, et al., "Consequences of Antisense RNA Inhibition of Starch Branching Enzyme Activity on Properties of Potato Starch," Carbohydrate Polymers 35: 155-168 (1998).
Sathish et al. "Cloning and Anti-Sense RNA Constructs of a Startch Branching Enzyme Gene From Barley Endosperm." Photosynthesis: from Light to Biosphere vol. V. P. Mathis (ed.) pp. 313-316 (1995).
Schondelmaier et al., "Genetical Studies in the Mode of Inheritance and Localization of the amol (High Amylose) Gene in Barley," Plant Breeding 109: 274-280 (1992).
Schwall, et al., "Production of Very-High-Amylose Potato Starch by Inhibition of SBE A and B," Nature Biotechnology 18: 551-554 (2000).
Shannon and Garwood, "In Starch: Chemistry and Technology," Whistler et al., eds, Academic Press, Orlando, FL, 25-86 (1984).
Sidebottom, et al., "Characterization of the Difference of Starch Branching Enzyme Activities in Normal and Low-Amylopectin Maize during Kernel Development," Journal of Cereal Science 27: 279-287 (1998).
Sun et al., "Identification of Four Starch-Branching Enzymes in Barley Endosperm: Partial Purification of forms I, II a and IIb." New Phytol. 137:215-222 (1997).
Sun et al., "The Two Genes Encoding Startch-Branching Enzymes IIa and IIb are Differentially Expressed in Barley," Plant Physiology 118:37-49 (1998).
Sundberg et al., "Glycaemic Responses and Hypocholesterolaemic Effects of High-Amylose Barley Diets on Broiler Chicks," J. Sci. Food Agric. 76: 457-463 (1998).
Takaoka, M, et al., "Structural characterization of high molecular weight starch granule-bound proteins in wheat (Triticum aestivum L.)," J. Agric. Food Chem. 45: 2929-2934(1997).
Terada et al., "Efficient Gene Targeting by Homologous Recombination in Rice," Nature Biotech. 20:1030-1034 (1997).
Tetlow et al. "Recent developments in understanding the regulation of starch metabolism in higher plants," Journal of Experimental Botany 55(406):2131-2145 (2004).
Thomas, et al., "Size Constraints for Targeting Post-Transcriptional Gene Silencing and for RNA-directed Mehtylation in Nicotiana benthamiana Using a Potato Virus X Vector," Plant J. 25: 417-425 (2001).
Van der Leij et al., "Sequence of the Structural Gene for Granule-Bound Starch Synthase of Potato (Solanum Tuberosum L.) and Evidence for a Single Point Deletion in the amf allele," Mol. Gen. Genet. 228: 240-248 (1991).
Vrinten and Nakamura, "Wheat Granule-Bound Starch Synthase I and II are Encoded by Separate Genes That Are Expressed in Different Tissues," Plant Physiology 122:255-263 (2000).
USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System Accession No. GSHO 2476, Jun. 23, 1997).
Walker and Meritt, "Genetic Control of Abnormal Starch Granules and High Amylose Content in a Mutant of Glacier Barley," Nature 221:482-484 (1969).
Yamamori et al., "Genetic Elimination of a Starch Granule Protein, SGP-1, of Wheat Generates an Altered Starch with Apparent High Amylose," Theor. Appl. Genet. 101: 21-29 (2000).
Yamamori and Endo, "Variation of Starch Granule Proteins and Chromosome Mapping of Their Coding Genes in Common Wheat," Theor. Appl. Genet. 93: 275-181 (1996).

Yamamori, "Selection of a Wheat Lacking a Putative Enzyme for Starch Synthesis, SGP-1," Proc. 9th in Wheat Gen. Symp. 4:300-302 (1998).
Abel et al., GenBank Accession #Y10416 (Jan. 1997) S. Tuberosum mRNA for Soluble Starch Synthase.
Bhullar et al., GenBank Accession #CAB40374 (Apr. 1999) Starch synthase isoform SS III [Vigna unguiculata].
Block et al., GenBank Accession #U48227 (Jun. 1996) Triticum aestivum soluble starch synthase mRNA, partial cds.
D'Hulst et al., GenBank Accession #AAC17969 (Nov. 2001) Granule-bound starch synthase I precursor [Chlamydomonas reinhardtii].
Gao et al., GenBank Accession #AAC14014 (Apr. 1998) Starch synthase DULL 1 [Zea mays].
Gao et al., GenBank Accession #AAC14015 (Apr. 1998) Starch synthase DULL 1 [Zea mays].
Gao et al., GenBank Accession #CAB86618 (Apr. 2002) Starch synthase IIa-1 [Triticum aestivum].
Gao et al., GenBank Accession #AJ269502 (Apr. 2002) Triticum aestivum MRNA for starch synthase II a-1 (wSs2a-1 gene).
Rahman et al., GenBank Accession #AF076680 (May 1999) Aegilops tauschii starch branching enzyme-I (SBE-I) gene, complete cds.
Walter et al., GenBank Accession #AAB17085 (Oct. 1996) Starch Synthase.
Walter at al., GenBank Accession #U66377 (Oct. 1996) Triticum aestivum soluble starch synthase mRNA, partial cds.
International Search Report issued by the International Searching Authority (ISA/AU) on Feb. 10, 2005 in connection with International Application No. PCT/AU2004/001517.
Australian Patent Publication Application No. AU 2004284112 A1, published May 25, 2006, Li et al.
Chinese Patent Application Publication No. CN 1886507 A, published Dec. 27, 2006, Li et al.
First Official Action, issued Jul. 4, 2008, in connection with Chinese Patent Application Publication No. 1886507 with English Translation.
Amendment in Response to Jul. 4, 2008 Official Action, issued in connection with Chinese Patent Application Publication No. 1886507, filed Nov. 18, 2008.
Second Official Action, issued Dec. 18, 2009, in connection with Chinese Patent Application Publication No. 1886507 with English Translation.
Clarke at al., (2008) Gene expression in a starch synthase IIa mutant of barley: changes in the level of gene transcription and grain composition. Functional Integrated Genomics, 8:211-221.
Fujita at al., (2007) Characterization of SSIIIa-Deficient Mutants of Rice: The Function of SSIIIa and Pleiotropic Effects by SSIIIa. Deficiency in the Rice Endosperm. Plant Physiology, 144: 2009-2023.
Fujita et al., (2003) Antisense Inhibition of Isoamylase Alters the Structure of Amylopectin and the Physiochemical Properties of Starch in Rice Endosperm. Plant Cell Physiol. 44(6):607-618.
Li et al., (2011) The barley amol locus is tightly linked to the starch synthase IIIa gene and negatively regulates expression of granule-bound starch synthetic genes. Journal of Experimental Botany 62: 5217-5231.
Li et al., (2003) the structural organisation of the gene encoding class II starch synthase of wheat and barley and the evolution of the genes encoding starch synthases in plants. Funct Integr Genomics 3:76-85.
Liu et al., (2003) Stable Inheritance of the Antisense Waxy Gene in Transgenic Rice with Reduced Amylose Level and Improved Quality. Transgenic Research, 12:71-82.
Lorberth at al., (1998) Inhibition of a starch-granule-bound protein leads to modified starch and repression of cold sweetening. Nature Biotechnology, 16(1):473-477.
Newman et al., (1978) Comparative Nutritive Value of Glacier and High Amyliose Glacier Barleys. Journal of Animal Science, 47:448-456.
Sestili et al., (2010) Increasing the amylase content of durum wheat through silencing of the SBEIIa genes. BMC Plant Biol. 10:144.
Slade et al., (2012) Development of High Amylose Wheat Through TILLING. BMC Plant Biology, 12:69-100.

(56) References Cited

OTHER PUBLICATIONS

Wasserman et al., (2004) Microstructure, Thermal properties and susceptibility of the high amylose wheat starch to enzymatic hydrolysis: A new material for resistant starch (SSIII) production. Polish Journal of Food and Nutrition Sciences vol. 13-54, No. 2, pp. 151-156.

Wei et al., (2010) C-Type Starch from High-Amylose Rice Resistant Starch Granules Modified by Antisense RNA Inhibition Starch Branching Enzyme. Journal of Agricultural and Food Chemistry, 58: 7383-7388.

Zhang et al., (2008) Overlapping functions of the starch synthases SSII and SSIII in amylopectin biosynthesis in Arabidopsis. BMC Plant Biology 8:96.

Zabel et al., (1988) Starch Gelatinization: An X-ray Diffraction Study. Cereal Chem, 65(6):443-446.

Zobel, H.F., (1988) Starch Crystal Transformations and Their Industrial Importance. Starch, 40(1): 1-7.

Zwar and Chandler, (1995) α-Amylose production and leave protein synthesis in a gibberellin-responsive dwarf mutant of 'Himalaya' barley (Hordeum vulgare L.). Planta, 197:39-48.

File History of U.S. Patent Application Publication No. 2011-0281618, Jenkins et al., published Nov. 17, 2011.

File History of U.S. Patent Application Publication No. 2011-0045127, Ral et al., published Feb. 24, 2011.

File History of U.S. Patent Application Publication No. 2012-0074247, Regina et al., published Mar. 29, 2012 (U.S. Appl. No. 13/243,220).

File History of U.S. Patent Application Publication No. 2012-0114770, Regina et el., published May 10, 2012.

File History of U.S. Patent Application Publication No. 2013-0158924, Morell et al., published Jun. 20, 2013.

File History of U.S. Patent Application Publication No. 2012-0129805, Li et al., published May 24, 2012.

```
   1 GCCACCGACA TCCGCCGCAA TGCTGTGTCT CACCTCCTCT TCCTCCTCCG CGCCCGCTCC
  61 GCTCCTTCCC TCTCTCGCTG ATCGACCGAG CCCGGGAATC GCGGGCGGGG GTGGCAATGT
 121 TCGCCTGAGC GTGGTTTCTT CGCCGCGCCG GTCGTGGCCT GGAAAGGTCA AGACCAATTT
 181 CTCAGTTCCT GCGACTGCGC GAAAAAACAA AACCATGGTG ACTGTTGTGG AGGAGGTCGA
 241 CCACCTTCCT ATATATGATC TGGACCCTAA GTTGGAGGAA TTCAAGGATC ACTTCAACTA
 301 TAGGATAAAA AGATACCTCG ACCAGAAATG CCTGATTGAA AAACATGAGG GGGGCCTTGA
 361 AGAATTTTCT AAAGGCTATT TGAAGTTTGG GATTAATACA GTTGATGGTG CCACAATATA
 421 TCGTGAATGG GCGCCTGCTG CACAAGAAGC ACAGCTCATT GGTGAGTTCA ATAACTGGAA
 481 TGGTGCAAAA CACAAGATGG AGAAGGATAA ATTTGGCATT TGGTCAATCA AGATTTCACA
 541 TGTCAATGGG AAGCCTGCCA TCCCTCACAA TTCCAAGGTT AAATTTCGCT TTAGGCATGG
 601 GGGTGGAGCA TGGGTTGATC GTATTCCCGC ATGGATTCGT TATGCAACTT TTGATGCCTC
 661 TAAATTTGGA GCTCCATATG ATGGTGTACA CTGGGATCCT CCAGCCTGTG AAAGGTACGT
 721 GTTTAAGCAT CCTCGACCTC CAAAACCTGA TGCTCCACGC ATCTATGAGG CTCATGTGGG
 781 GATGAGTGGT GAAGAGCCAG AAGTAAGCAC ATACAGAGAA TTTGCAGACA ATGTGTTACC
 841 ACGCATACGG GCAAATAACT ACAACACAGT TCAGTTAATG GCAATCATGG AACATTCCTA
 901 CTATGCTTCT TTTGGGTATC ACGTGACAAA TTTTTTCGCA GTCAGCAGCA GATCAGGAAC
 961 ACCAGAGGAT CTGAAATATC TTGTTGACAA GGCACATAGT TTAGGATTAC GAGTTCTGAT
1021 GGATGTTGTC CATAGCCATG CGAGTAATAA TGTGACCGAT GGTCTAAATG GCTATGACGT
1081 TGGACAAAAC ACTCATGAGT CTTATTTTCA TACAGGAGAT AGGGGCTACC ATAAACTCTG
1141 GGATAGTCGT CTGTTCAACT ATGCCAATTG GGAGGTCTTA AGATTTCTTC TTTCTAATTT
1201 GAGATATTGG ATGGACGAAT TCATGTTTGA TGGCTTCCGA TTTGATGGGG TTACATCAAT
1261 GCTATACCAT CACCATGGTA TCAATAAGGG ATTTACTGGA AACTACAAGG AGTATTTCAG
1321 TTTGGATACC GATGTGGATG CAATTGTTTA CATGATGCTC GCAAACCATT TAATGCATAA
1381 ACTCTTGCCG GAAGCAACTA TTGTTGCTGA AGATGTTTCG GGCATGCCAG TGCTTTGTCG
1441 GCCAGTTGAT GAAGGTGGAG TAGGGTTTGA CTTCCGCCTG GCAATGCCA TTCCTGATAG
1501 ATGGATTGAC TACCTGAAGA ACAAAGAGGA CCGCAAATGG TCAATGAGTG AAATAGTGCA
1561 AACTTTGACT AACAGGAGAT ATACAGAAAA ATGCATTGCC TATGCCGAGA GCCATGATCA
1621 GTCCATTGTT GGTGACAAGA CTATAGCATT TCTCTTGATG GACAAGGAAA TGTACACTGG
1681 CATGTCAGAC TTGCAGCCTG CTTCACCTAC CATCAACCGT GGCATTGCAC TCCAAAAGAT
1741 GATTCACTTC ATTACGATGG CCCTTGGAGG TGATGGCTAC TTAAATTTTA TGGGCAATGA
1801 GTTTGGCCAT CCAGAATGGA TTGACTTTCC AAGAGAAGGC AACAACTGGA GCTATGATAA
1861 ATGCAGACGT CAGTGGAGCC TTGTCGACAC TGATCACCTT CGATACAAGT ATATGAATGC
1921 ATTTGATCAA GCAATGAATG CACTCGAGGA GGAATTTTCC TTCCTGTCAT CATCAAAGCA
1981 GATTGTTAGC GACATGAACG AGAAAGATAA GGTTATTGTC TTTGAACGTG GAGATTTGGT
2041 TTTTGTTTTC AATTTTCATC CCAACAAAAC TTACAAGGGT TACAAAGTCG GATGTGACTT
2101 GCCCGGGAAG TACAGAGTAG CTCTGGACTC TGATGCTTTG GTCTTTGGTG GCCATGGAAG
2161 AGTTGCCCAT GATGTGGATC ACTTCACGTC TCCCGAGGGA ATGCCAGGAG TACCAGAAAC
2221 AAATTTCAAC AACCGCCCTA ACTCATTCAA AGTCCTTTCC CCGCCCCGTA CCTGTGTGGC
2281 TTACTATCGC GTTGATGAAG ATCGTGAAGA GCTCAGGAGG GGTGGAGCAG TTGCTTCTGG
2341 AAAGATTGTT ACAGAGTATA TCGATGTTGA AGCAACAAGT GGGGAGACTA TCTCTGGTGG
2401 CTGGAAGGGC TCCGAGAAGG ACGATTGTGG CAAGAAAGGG ATGAAGTTTG TGTTTCGGTC
2461 TTCTGACGAA GACTGCAAAT GAAGCATCAG ATTTCTTGAT CAGGAGCAAC TGTTGGTGCC
2521 CTTGTAATCT GGAGATCCTG GCTTGCCTTG GACTTGGTTG TGGTTCTTTA GCAGTTGCTA
2581 TGTACCTATC TATGATATGA ACTTTATGTA TAGTTCGCCT TAAAGAAAGA ATAAGCAGTG
2641 ATGATGTGGC CTTAAACCTG AGCTGCACAA GCCTAATGTA AAAATAAAGT TTCAGGCTTT
2701 CATCCAGAAT AAAACAGCTG TTCATTTACC ATCTCAAAA
```

Figure 1

```
   1 CTTGACTCCC CCCACTCCTC CCTCGTGCTG CTCCTCCTCG TCGCTCGGCT CGAGGCGCGG
  61 CATTTGCGGC GGGAGGGATC TGCGCGCGAG TGCGTGCGGG CAGGCGGCGG GGGAGCACGC
 121 ACCGGGGGAT GGCGTCGTTC GCGGTGTCCG GCGCGAGGCT CGGGGTCGTG CGGGCGGGGG
 181 GCGGCGGCGG CGGCGGGGGT GGCCCGGCGG CGCGATCCGG CGGGGTGGAC TTGCCGTCGG
 241 TGCTCTTCAG GAGGAAGGAC TCCTTCTCAC GTGGCGTTGT GAGCTGCGCG GGTGCTCCTG
 301 GGAAGGTGCT GGTGCCTGGC GGTGGGAGCG ACGACTTGCT GTCCTCTGCG GAACCAGACG
 361 TGGAAACTCA AGAGCAACCT GAAGAATCTC AGATACCTGA TGATAATAAA GTAAAACCTT
 421 TTGAGGAGGA GGAAGAGATT CCAGCAGTGG CAGAAGCAAG CATAAAGGTT GTGGCTGAAG
 481 ACAAACTTGA ATCTTCAGAA GTGATTCAAG ACATTGAGGA AAATGTGACT GAGGGTGTGA
 541 TCAAAGATGC TGATGAACCA ACTGTGGAGG ATAAACCACG AGTTATCCCA CCACCAGGAG
 601 ATGGGCAGAA GATATACCAA ATTGACCCAA TGCTGGAAGG ATTTCGGAAC CATCTTGACT
 661 ACCGATACAG TGAATACAAG AGAATGCGTG CAGCTATTGA CCAACATGAA GGTGGCTTGG
 721 ATGCATTTTC TCGTGGTTAC GAAAAGCTTG GATTCACCCG CAGCGCTGAA GGCATTACCT
 781 ACCGAGAATG GGCACCTGGA GCACAGTCTG CAGCATTAGT AGGTGACTTC AACAATTGGA
 841 ACCCAAATGC AGATACTATG ACCAGAAATG AGTATGGTGT TTGGGAGATT TCCCTGCCTA
 901 ACAATGCTGA TGGATCCCCT GCTATTCCTC ATGGCTCACG TGTAAAGATT CGGATGGATA
 961 CACCATCTGG CGTAAAGGAT TCAATTCCTG CCTGGATTAA GTTTGCTGTG CAGGCTCCAG
1021 GTGAAATACC GTACAACGGT ATATATTATG ATCCACCTGA AGAAGAAAAA TATGTATTCC
1081 AACATCCTCA ACCTAAACGA CCAAATTCGC TGCGGATATA TGAATCACAT ATTGGAATGA
1141 GTAGCCCGGA ACCGAAGATA AACACATATG CTAATTTTAG GGATGAGGTG CTACCAAGAA
1201 TTAAAAAGCT TGGGTACAAT GCTGTACAGA TAATGGCAAT CCAGGAGCAC TCTTATTACG
1261 CAAGCTTTGG GTATCATGTT ACTAACTTCT TTGCGCCAAG TAGCCGTTTC GGAACCCCAG
1321 AAGACTTGAA ATCTCTGATT GATAAAGCTC ACGAGCTTGG TTTGCTTGTA CTTATGGATA
1381 TTGTTCACAG TCATGCATCA AACAATACCC TGGATGGTTT GAATGGTTTT GATGGTACTG
1441 ATACACATTA CTTCCATGGT GGACCACGGG GTCATCACTG GATGTGGGAT TCTCGCCTGT
1501 TCAACTATGG GAGTTGGGAA GTTTTAAGAT ATTTACTGTC GAATGCAAGG TGGTGGCTTG
1561 AAGAATACAA GTTTGATGGG TTTCGATTTG ATGGGGTGAC CTCCATGATG TATACTCATC
1621 ATGGTTTACA GGTGGCATTT ACTGGCAACT ATGGCGAATA TTTTGGATTT GCTACTGATG
1681 TTGATGCAGT AGTTTACTTG ATGCTGGTGA ACGATCTAAT TCATGGGCTT TATCCTGAGG
1741 CTGTAGCCAT TGGTGAAGAT GTCAGCGGGA TGCCCACATT TTGTATTCCT GTTCAAGATG
1801 GTGGTGTTGG TTTTGACTAT CGTTTGCATA TGGCTGTACC GGACAAATGG ATCGAACTCC
1861 TCAAGCAAAG TGACGAATAT TGGAAAATGG GTGATATCGT GCACACCCTA ACGAATAGAA
1921 GGTGGTCAGA GAAGTGTGTT ACTTATGCAG AAAGTCATGA CCAAGCACTA GTTGGTGACA
1981 AGACTATTGC ATTCTGGTTG ATGGATAAGG ATATGTATGA TTTTTATGGT CTAGACAGAC
2041 CTTCAACACC TCGCATTGAT CGTGGGATAG CATTACATAA AATGATTAGG CTTGTCACCA
2101 TGGGCTTAGG AGGCGAAGGC TATCTTAATT TCATGGGAAA TGAGTTTGGG CATCCTGAAT
2161 GGATAGATTT CCCAAGAGGC CGCAAAGTC TTCCAAATGG CTCGGTCCTC CCAGGAAACA
2221 ACTACAGTTT TGATAAATGC CGTCGTAGAT TTGACCTTGG AGATGCAGAT TATCTTAGAT
2281 ATCATGGTAT GCAAGAGTTT GATCAGGCCA TGCAGCATCT TGAGGAAAAA TATGGATTCA
2341 TGACATCTGA GCACCAGTAT ATATCGCGCA AACACGAGGA GGATAAGGTG ATCATCTTCG
2401 AGAGAGGAGA TTTGGTATTC GTGTTCAACT TCCACTGGAG TAATAGCTAT TTTGACTATC
2461 GCGTCGGTTG TTTAAAGCCT GGAAAGTACA AGATTGTGTT GGACTCAGAC GATGGCCTCT
2521 TTGGTGGATT CAGTCGGCTT GATCATGATG CTGAGTACTT CACTGCTGAC TGGCCGCATG
2581 ACAACAGACC ATGTTCATTC TCGGTGTACA CCCCAAGCAG AACCGCCGTC GTGTATGCAC
2641 TTACAGAGGA CTAATGATCA GCTCTGATCA TTGGGGAAC AACTCAAGGG AGTTGGTGGT
2701 AATGACGCCG GAATACAACT CAAGTGAAAG GTGAAAAGAA AGGCTGCCCT GACGATGTGA
2761 TTTGAGGGGC TTGTGTTTCA TCGCCAATGC CAGGAAGATG AGGTAGAAAA GCCTACTGAT
2821 GAGCTCCTGT TTTCGAGTGA CTCGTGAAGG AAATAGACCA GGGTGAACGG CTTTTTTCAG
2881 AGCTATACCA AACCCATCCT ATGTTGCGCA TTCGCTGTAG TTTTGTACAT AACGATATCG
2941 GTTGGCATTT GTATGTTTAT GAATAATCTG TTCGACAGAA ATGTTTTTCT CCTTGTATTT
3001 AGTGCTCAAA AAAAA
```

Figure 2

```
   1 CGGCGCACAC CCACACACCG ACCACCAGGC AGCGCCTCCT CGCTTTGGCT CTCGCGTGAG
  61 GAGGGTTTAG GTGGAAGCAG AGCGCGGGGG TTGCCGGGGG ATCCGATCCG GCTGCGGTGC
 121 GGGCGAGATG GCGGCGCCGG CGTCTGCGGT TCCCGGAGC GCGGCGGGGC TACGGGCGGG
 181 GGCCGTGCGG TTCCCCGTGC CAGCCGGGGC CCGGAGCTGG CGTGCGGCGG CGGAGCTCCC
 241 GACGTCGCGG TCGCTGCTCT CCGGCCGGAG ATTCCCCGGT GCCGTTCGCG TGGGGGGTTC
 301 CGGGGGGCGC GTGGCCGTGC GCGCGGCGGG CGCGTCAGGG GAGGTGATGA TCCCCGAGGG
 361 CGAGAGCGAC GGGATGCCGG TTTCAGCAGG TTCAGACGAT CTGCAGTTGC CAGCCTTAGA
 421 TGATGAATTA AGCACGGAGG TTGGAGCTGA AGTTGAGATT GAGTCATCTG GAGCAAGTGA
 481 CGTTGAAGGC GTGAAGAGAG TGGTTGAAGA ATTAGCTGCT GAGCAGAAAC CACGAGTTGT
 541 CCCACCAACA GGAGATGGGC AAAAAATATT CCAGATGGAC TCTATGCTTA ATGGCTATAA
 601 GTACCATCTT GAATATCGAT ATAGCCTATA TAGGAGACTG CGTTCAGACA TTGATCAGTA
 661 TGAAGGAGGA CTGGAAACAT TTTCTCGCGG TTATGAGAAG TTTGGATTTA ATCACAGTGC
 721 TGAAGGTGTC ACTTATCGAG AATGGGCTCC CGGGGCACAT TCTGCAGCAT TAGTAGGTGA
 781 CTTCAACAAT TGGAATCCAA ATGCAGACCG CATGAGCAAA AATGAGTTTG GTGTTTGGGA
 841 GATTTTTCTG CCTAACAATG CTGATGGCTC ATCTCCTATT CCACATGGCT CACGTGTAAA
 901 GGTGCGAATG GAAACTCCAT CTGGTATAAA GGATTCTATT CCTGCCTGGA TCAAGTACTC
 961 TGTGCAGGCC GCAGGAGAAA TCCCATACAA TGGAATATAT TATGATCCTC CTGAAGAGGA
1021 GAAGTACATA TTCAAGCATC CTCAACCTAA AAGACCAAAG TCATTGCGGA TATACGAAAC
1081 TCATGTTGGA ATGAGTAGCA CGGAGCCAAA GATCAACACG TATGCAAACT TTAGGGATGA
1141 GGTGCTTCCA AGAATCAAAA AGCTTGGATA CAATGCAGTG CAAATAATGG CAATTCAAGA
1201 GCATGCATAT TATGGAAGCT TTGGGTACCA TGTCACCAAT TTCTTTGCAC CAAGTAGTCG
1261 TTTCGGGACC CCAGAAGATT TAAAGTCATT GATTGATAAA GCTCATGAGC TTGGTTTAGT
1321 TGTGCTCATG GATGTTGTTC ACAGCCATGC GTCAAATAAT ACCCTAGATG GGTTGAACGG
1381 TTTTGATGGT ACAGATACGC ATTACTTTCA TAGTGGTTCA CGCGGCCATC ATTGGATGTG
1441 GGATTCTCGC CTTTTCAACT ATGGGAATTG GGAAGTTCTA AGATTTCTAC TATCCAATGC
1501 AAGATGGTGG CTCGAGGAGT ATAAGTTTGA TGGTTTCAGA TTTGACGGTG TAACCTCAAT
1561 GATGTACACT CATCATGGAT TACAAGTAGC ATTTACGGGG AACTACAGTG AATACTTTGG
1621 ATTTGCCACT GATGCTGATG CAGTAGTTTA CTTGATGCTG GTAAATGATT TAATTCATGG
1681 ACTTTATCCT GAGGCCATAA CCATCGGTGA AGATGTCAGT GGAATGCCTA CATTTGCCCT
1741 TCCTGTTCAA GATGGTGGGG TTGGTTTTGA TTATCGCCTT CATATGGCTG TTCCTGACAA
1801 ATGGATTGAA CTCCTCAAGC AAAGTGATGA ATCTTGGAAG ATGGGTGATA TTGTGCACAC
1861 ACTGACTAAC AGAAGGTGGT CAGAGAAGTG TGTTACTTAT GCTGAAAGTC ATGATCAAGC
1921 ACTAGTTGGT GACAAAACTA TTGCATTCTG GTTGATGGAC AAGGATATGT ATGATTTTAT
1981 GGCTCTGGAC AGACCGGCAA CACCTAGCAT TGATCGTGAA ATAGCATTGT ATAAAATGAT
2041 TAGACTTATC ACAATGGGGT TAGGAGGAGA AGGCTATCTT AACTTTATGG GAAATGAGTT
2101 CGGACATCCT GAATGGATTG ATTTTCCAAG AGCTCCACAA GTACTTCAA ATGGTAAATT
2161 CATCCCAGGG AATAACAACA GTTATGATAA ATGCCGTCGA AGATTTGACC TGGGTGATGC
2221 GGACTATCTT AGGTATCGTG GCATGCTAGA GTTTGACCGC GCGATGCAGT CTCTCGAGGA
2281 AAAATATGGG TTCATGACAT CAGACCACCA GTACATATCT CGAAAGCATG AAGAGGATAA
2341 GATGATTATA TTTGAGAAGG GAGATCTGGT ATTTGTGTTC AACTTCCATT GGAGTAACAG
2401 CTATTTTGAC TACCGTGTTG GTTGTTTAAA GCCAGGGAAA TATAAGGTGG TCTTGGACTC
2461 AGATGCTGGA CTCTTTGGTG GATTTGGCAG GATCCATCAC ACTGCAGAGC ACTTCACTGC
2521 CGATTGTTCA CATGACAACA GGCCCTACTC GTTCTCAGTT TATTCTCCTA GCAGAACCTG
2581 CGTTGTCTAT GCTCCAGCGG AATGAGAACA CCAAGAGGCA GCATGCAAGT GTGTGCGGCT
2641 GCTAGTGCGA AGGAGCAAGA AAAACTAGTT GCCAGCAATC TGTGAACGGC TTTCCTAGGT
2701 TCTGCTTCGA TGAATGCCGG ATAGACTAGA CAGCTTGCTT TTGTGCTTTG CGCTCCCAAT
2761 TTGTAGTTTT AGTTTGTGAG GGAAAGAAAC GTTTATTTGT AATTATCTAT GGCTGTCGAA
2821 CGGCGACGAA ACCATGAACC CCGTATATTT GTTGGTACCG TTCGAACTGC CAGTTATACA
2881 TAGTTCTGCA CTTCTGTACA TCTTGTGATG CTTGAATC
```

Figure 3

```
 82 GCGCGGGGGTTGCCGGGGGATCCGATCCGGCTGCG.GTGCGGGCGAGATG 130
    ||||||    ||||  |||||    ||||  |    ||| |||||  |||  |   |
 55 gcgcggcatttgcggcggga.gggatctgcgcgcgagtgcgtgcgggcag 103

131 GCGGC.....................GCCGGCGTCTGCGGTTCCCGGGA 158
    |||||                     |  || |||  |||||   ||  ||
104 gcggcgggggagcacgcaccgggggatggcgtcgttcgcggtgtcc.ggc 152

159 GCGCGGCGGGGCTACGGGCGGGGGCCGTGCGGTTCCCCGTGCCAGCCGGG 208
    ||| |||  ||   || ||||||  |   ||||    |  |  || |||
153 gcgaggctcggggtcgtgcgggcggggggcgg....cggcggcggcgggg 198

209 GCCCGGAGCTGGCGTGCGGCGGCGGAGCTCCCGACGTCGCGGTCGCTGCT 258
    |     |  ||||  |   ||||||  |||||||              
199 gtggcccggcggcgcgatccggcgggg....tggacttgccgtcggtgct 244

259 CTCCGGCCGGAGATTCCCCGGTGCCGTTCGCGTGGGGGGTTCCGGGGGC 308
    ||  |  |  |||              ||    |  ||  |  ||  |||
245 cttcaggagga.......aggactccttctcacgtggcgtt......... 278

309 GCGTGGCCGTGCGCGCGGCGGGCGCGTCAGGGGAGGTGATGATCCCCGAG 358
                ||| ||  ||||| ||  | ||| ||||| ||  ||  |
279 ........gtgagctgcgcgggtgctcctgggaaggtgctggtgcctggc 320

359 GGCGAGAGCGACGGGATGCCGGTTTCAGCAGGTTCAGACG.......... 398
    || |  ||||||||||   ||| |   || || |    ||||||
321 ggtgggagcgacgacttgctgtcctctgcggaaccagacgtggaaactca 370

399 ................ATCTGCAGTTGCC................AGCCT 416
                    ||||  |||  ||                |  |||
371 agagcaacctgaagaatct.cagatacctgatgataataaagtaaaacct 419

417 T.......................AGATGATGAATTAAGCACGGAGGT 441
    |                       ||   |   |||   |||||    ||||
420 tttgaggaggaggaagagattccagcagtggcagaagcaagcataaaggt 469

442 TGGAGCTGAAGTTGAGATTGAGTCATC................TGGAG 473
    ||  |||||||       |    ||||  ||  ||                     ||   |
470 tgtggctgaagacaaacttgaatcttcagaagtgattcaagacattgagg 519

474 CAAGTGACGTTGAAGGCGTGAAGAGAGTGGTTGAAGAATTAGCTGCTGAG 523
    ||  ||      ||| ||  |||| |  ||  |  |||| |||  | |||   |||
520 aaaatgtgactgagggtgtgatcaaagatgctgatgaaccaactgtggag 569

524 CAGAAACCACGAGTTGTCCCACCAACAGGAGATGGGCAAAAAATATTCCA 573
    |  |||||||||||||| |||||||||  ||||||||||||||||  ||||  |||
570 gataaaccacgagttatcccaccaccaggagatgggcagaagatatacca 619

574 GATGGACTCTATGCTTAATGGCTATAAGTACCATCTTGAATATCGATATA 623
    ||  ||||  |||||  |  ||  |  |  | |||||||||||  ||||||  |
620 aattgacccaatgctggaaggatttcggaaccatcttgactaccgataca 669

624 GCCTATATAGGAGACTGCGTTCAGACATTGATCAGTATGAAGGAGGACTG 673
    |    ||||  |||||  |||||  ||| |||  |||||||  ||  ||||||  ||  ||
670 gtgaatacaagagaatgcgtgcagctattgaccaacatgaaggtggcttg 719
```

Figure 7

```
 674 GAAACATTTTCTCGCGGTTATGAGAAGTTTGGATTTAATCACAGTGCTGA  723
     ||  ||||||||||| |||||| ||  ||| |||||||  |  ||| |||||
 720 gatgcattttctcgtggttacgaaaagcttggattcacccgcagcgctga  769

724 AGGTGTCACTTATCGAGAATGGGCTCCCGGGGCACATTCTGCAGCATTAG  773
     |||   | ||  || ||||||||||  || ||  |||| |||||||||||
 770 aggcattacctaccgagaatgggcacctggagcacagtctgcagcattag  819

774 TAGGTGACTTCAACAATTGGAATCCAAATGCAGACCGCATGAGCAAAAAT  823
     |||||||||||||||||||||||| |||||||||||   |||| ||  ||||
 820 taggtgacttcaacaattggaacccaaatgcagatactatgaccagaaat  869

824 GAGTTTGGTGTTTGGGAGATTTTTCTGCCTAACAATGCTGATGGCTCATC  873
     ||||  |||||||||||||||| |||||||||||||||||||||||  |
 870 gagtatggtgtttgggagatttccctgcctaacaatgctgatggatcccc  919

874 TCCTATTCCACATGGCTCACGTGTAAAGGTGCGAATGGAAACTCCATCTG  923
     |  ||||||| |||||||||||||||||| | || |||||| || ||||||
 920 tgctattcctcatggctcacgtgtaaagattcggatggatacaccatctg  969

924 GTATAAAGGATTCTATTCCTGCCTGGATCAAGTACTCTGTGCAGGCCGCA  973
     |   |||||||||| |||||||||||||||| ||||    |||||||||  ||
 970 gcgtaaaggattcaattcctgcctggattaagtttgctgtgcaggctcca 1019

974 GGAGAAATCCCATACAATGGAATATATTATGATCCTCCTGAAGAGGAGAA 1023
     ||  ||||| || |||| ||  |||||||||||||||| |||||||| || ||
1020 ggtgaaataccgtacaacggtatatattatgatccacctgaagaagaaaa 1069

1024 GTACATATTCAAGCATCCTCAACCTAAAAGACCAAAGTCATTGCGGATAT 1073
     ||  ||||| | |||||||||||||||||||| ||||||| ||  |||||||||
1070 atatgtattccaacatcctcaacctaaacgaccaaattcgctgcggatat 1119

1074 ACGAAACTCATGTTGGAATGAGTAGCACGGAGCCAAAGATCAACACGTAT 1123
     |  ||| ||| ||||||||||||||||  | ||||| || ||||| |||  |||
1120 atgaatcacatattggaatgagtagcccggaaccgaagataaacacatat 1169

1124 GCAAACTTTAGGGATGAGGTGCTTCCAAGAATCAAAAAGCTTGGATACAA 1173
     || ||  ||||||||||||||||||||||||||| |||||||||||||  |||||
1170 gctaattttagggatgaggtgctaccaagaattaaaaagcttgggtacaa 1219

1174 TGCAGTGCAAATAATGGCAATTCAAGAGCATGCATATTATGGAAGCTTTG 1223
     |||  || || |||||||||||| |||||| ||  | |  |||||||||| ||||||||
1220 tgctgtacagataatggcaatccaggagcactcttattacgcaagctttg 1269

1224 GGTACCATGTCACCAATTTCTTTGCACCAAGTAGTCGTTTCGGGACCCCA 1273
     ||||   |||||||  || || |||||||||| ||||||||| ||||||| |||||||
1270 ggtatcatgttactaacttctttgcgccaagtagccgtttcggaacccca 1319

1274 GAAGATTTAAAGTCATTGATTGATAAAGCTCATGAGCTTGGTTTAGTTGT 1323
     |||||   || || ||  ||||||||||||||||||||  ||||||||||||    ||||
1320 gaagacttgaaatctctgattgataaagctcacgagcttggtttgcttgt 1369

1324 GCTCATGGATGTTGTTCACAGCCATGCGTCAAATAATACCCTAGATGGGT 1373
     ||  ||||||| |||||||||||||| |||||  ||||| |||||||||| |
1370 acttatggatattgttcacagtcatgcatcaaacaatacccctggatggtt 1419
```

Figure 7 (continued)

```
1374 TGAACGGTTTTGATGGTACAGATACGCATTACTTTCATAGTGGTTCACGC 1423
     ||||  ||||||||||||  |||||  ||||||||  |||  ||||   ||||
1420 tgaatggttttgatggtactgatacacattacttccatggtggaccacgg 1469

1424 GGCCATCATTGGATGTGGGATTCTCGCCTTTTCAACTATGGGAATTGGGA 1473
     ||  ||||| ||||||||||||||||||||||||| |||||||||||||| ||||||
1470 ggtcatcactggatgtgggattctcgcctgttcaactatgggagttggga 1519

1474 AGTTCTAAGATTTCTACTATCCAATGCAAGATGGTGGCTCGAGGAGTATA 1523
     ||||  |||||||  |  ||||  ||  ||||||||| ||||||||  || || || |
1520 agttttaagatatttactgtcgaatgcaaggtggtggcttgaagaataca 1569

1524 AGTTTGATGGTTTCAGATTTGACGGTGTAACCTCAATGATGTACACTCAT 1573
     |||||||||  ||  ||||||| ||  || ||||| ||||||||  ||||||
1570 agtttgatgggtttcgatttgatggggtgacctccatgatgtatactcat 1619

1574 CATGGATTACAAGTAGCATTTACGGGGAACTACAGTGAATACTTTGGATT 1623
     |||||  ||||||  ||  |||||||||||  ||  |||||   ||||||  ||||||||
1620 catggtttacaggtggcatttactggcaactatggcgaatattttggatt 1669

1624 TGCCACTGATGCTGATGCAGTAGTTTACTTGATGCTGGTAAATGATTTAA 1673
     |||  |||||||  ||||||||||||||||||||||||||||||  ||  |||  |||
1670 tgctactgatgttgatgcagtagtttacttgatgctggtgaacgatctaa 1719

1674 TTCATGGACTTTATCCTGAGGCCATAACCATCGGTGAAGATGTCAGTGGA 1723
     ||||||||  |||||||||||||  ||  ||||  ||||||||||||  ||
1720 ttcatgggctttatcctgaggctgtagccattggtgaagatgtcagcggg 1769

1724 ATGCCTACATTTGCCCTTCCTGTTCAAGATGGTGGGGTTGGTTTTGATTA 1773
     |||||   ||||||           ||||||||||||||||||||||||||||||  ||
1770 atgcccacattttgtattcctgttcaagatggtggtgttggttttgacta 1819

1774 TCGCCTTCATATGGCTGTTCCTGACAAATGGATTGAACTCCTCAAGCAAA 1823
     |||  |  ||||||||||||  ||  ||||||||||| ||||||||||||||||||||||
1820 tcgtttgcatatggctgtaccggacaaatggatcgaactcctcaagcaaa 1869

1824 GTGATGAATCTTGGAAGATGGGTGATATTGTGCACACACTGACTAACAGA 1873
     ||||  ||||  ||||||  |||||||||  ||||||  |||   ||   |||
1870 gtgacgaatattggaaaatgggtgatatcgtgcacaccctaacgaataga 1919

1874 AGGTGGTCAGAGAAGTGTGTTACTTATGCTGAAAGTCATGATCAAGCACT 1923
     ||||||||||||||||||||||||||||||| |||||||||| |||||||||
1920 aggtggtcagagaagtgtgttacttatgcagaaagtcatgaccaagcact 1969

1924 AGTTGGTGACAAAACTATTGCATTCTGGTTGATGGACAAGGATATGTATG 1973
     ||||||||||||  |||||||||||||||||||||||| ||||||||||||||
1970 agttggtgacaagactattgcattctggttgatggataaggatatgtatg 2019

1974 ATTTTATGGCTCTGGACAGACCGGCAACACCTAGCATTGATCGTGGAATA 2023
     |||||||||||||| ||||||||  |||||||| ||||||||||||||||||  |||
2020 attttatggctctagacagaccttcaacacctcgcattgatcgtgggata 2069

2024 GCATTGCATAAAATGATTAGACTTATCACAATGGGGTTAGGAGGAGAAGG 2073
     |||||  |||||||||||||||  |||  ||||  ||||||  |||||||  ||||
2070 gcattacataaaatgattaggcttgtcaccatgggcttaggaggcgaagg 2119
```

Figure 7 (continued)

```
2074 CTATCTTAACTTTATGGGAAATGAGTTCGGACATCCTGAATGGATTGATT 2123
     ||||||||| || |||||||||||||| || ||||||||||||||| ||||
2120 ctatcttaatttcatgggaaatgagtttgggcatcctgaatggatagatt 2169

2124 TTCCAAGAGCTCCACAAGTACTTCCAAATGGTAAATTCATCCCAGGGAAT 2173
     | |||||||  || |||  ||||||||||||   || |||||||| ||
2170 tcccaagaggcccgcaaagtcttccaaatggctcggtcctcccaggaaac 2219

2174 AACAACAGTTATGATAAATGCCGTCGAAGATTTGACCTGGGTGATGCGGA 2223
     ||| |||||| |||||||||||||| ||||||||||||| || ||||||
2220 aactacagttttgataaatgccgtcgtagatttgaccttggagatgcaga 2269

2224 CTATCTTAGGTATCGTGGCATGCTAGAGTTTGACCGCGCGATGCAGTCTC 2273
     |||||||| |||| ||| |||| ||||||||| |  || |||||| ||
2270 ttatcttagatatcatggtatgcaagagtttgatcaggccatgcagcatc 2319

2274 TCGAGGAAAAATATGGGTTCATGACATCAGACCACCAGTACATATCTCGA 2323
     |  |||||||||||| ||||||||||||  || ||||||| ||||| ||
2320 ttgaggaaaaatatggattcatgacatctgagcaccagtatatatcgcgc 2369

2324 AAGCATGAAGAGGATAAGATGATTATATTTGAGAAGGGAGATCTGGTATT 2373
     ||  || || |||||||| |||| || || ||||| ||||| |||||||
2370 aaacacgaggaggataaggtgatcatcttcgagagaggagatttggtatt 2419

2374 TGTGTTCAACTTCCATTGGAGTAACAGCTATTTTGACTACCGTGTTGGTT 2423
     |||||||||||||||||||||| ||||||||||||||| || || ||||
2420 cgtgttcaacttccactggagtaatagctattttgactatcgcgtcggtt 2469

2424 GTTTAAAGCCAGGGAAATATAAGGTGGTCTTGGACTCAGATGCTGGACTC 2473
     ||||||||||  || || ||| | || |||||||||||  ||| |||||
2470 gtttaaagcctggaaagtacaagattgtgttggactcagacgatggcctc 2519

2474 TTTGGTGGATTTGGCAGGATCCATCACACTGCAGAGCACTTCACTGCCGA 2523
     ||||||||||  | ||| ||||  ||| ||| ||| |||||||| ||
2520 tttggtggattcagtcggcttgatcatgatgctgagtacttcactgctga 2569

2524 TTGTTCACATGACAACAGGCCCTACTCGTTCTCAGTTTATTCTCCTAGCA 2573
     || |  |||||||||||| || |  || ||||| || || | || ||||
2570 ctggccgcatgacaacagaccatgttcattctcggtgtacaccccaagca 2619

2574 GAACCTGCGTTGTCTATGCTC 2594
     ||||| ||| || ||||| |
2620 gaaccgccgtcgtgtatgcac 2640
```

Figure 7 (continued)

```
riceSBEIIaIR.seq

1    CTCGAGTCTA  GATCGCGTC G GTTGTTTA  AA GCCTGGA  AAG TACAAG  ATTGT
56   GTTGGACTC   AGACGATGGC  CTCTTTGGT G GATTCAGT  CG GCTTGAT  CATGA
111  TGCTGAGT A  CTTCACTGC   TGACTGGCCG  CATGACAAC  A GACCATGT  TCATT
166  CTCGGTG TA  CACCCCAA G  CAGAACCGC   CGTCGTGTAT  GCACTTACA  GAGGA
221  CTAATG ATC  AGCTCTG AT  CATTGGGG G  AACAACTCA   AGGGAGTTGG  TGGTA
276  ATGAC GCCG  GAATAC AAC  TCAAGTG AA  AGGTGAAA A  GAAAGGCTGC  CCTGA
331  CGAT GTGAT  TTGAG GGGC  TTGTGT TTC  ATCGCCA AT  GCCAGGAAGA  TGAGG
386  TAG AAAAGC  CTAC TGATG  AGCTC CTGT  TTTCGA GTG  ACTCGTGAAG  GAAAT
441  AG ACCAGGG  TGA ACGGCT  TTTT TCAGA  GCTAT ACCA  AACCCATCCT  ATGTT
496  G CGCATTCG  CT GTAGTTT  TGT ACATAA  CGAT ATCGG  TTGGCATTTG  TATGT
551   TTATGAATA A TCTGTTCG   AC AGAAATG  TTT TTCTCC  TTGTAACTAG  TGAA
606  TTC riceSBEIIbIR.seq 1    CTCGAGTCTA  GNNNNNNNN  N NNNNNNNN  NN NNNNNNN  NNN NNNNNNN NNNNN
56   NNNNNNNNNN  NNNNNNNNNN  NNNNNNNNN N NNNNNNNN  NN NNNNNNN NNNNN
111  NNNNNNNN N  NNNNNNNNN   NNNNNNNNNN  NNNNNNNN  N NNNNNNNN  NNNNN
166  NNNNNNN NN  NNNNNNNN N  NNNNNNNNNN  NNNNNNNNNG  CTCCAGCGG  AATGA
221  GAACAC CAA  GAGGCAG CA  TGCAAGTG T  GTGCGGCTG   CTAGTGCGAA  GGAGC
276  AAGAA AAAC  TAGTTG CCA  GCAATCT GT  GAACGGCT T  TCCTAGGTTC  TGCTT
331  CGAT GAATG  CCGGA TAGA  CTAGAC ANN  NNNNNNN NN  NNNNNNNNNN  NNNNN
386  NNT TGTAGT  TTTA GTTTG  TGAGG GAAA  GAAACG TTT  ATTTGTAATT  ATCTG
441  TG GCTGTCG  AAC GGCGAC  GAAA CCATG  AACCC CGTA  TATTTGTTGG  TACCG
496  T TCGAACTG  CC AGTTATA  CAT AGTTCT  GCAC TTCTG  TACATCTTGT  GATGC
551   TACTAGTGA A TTC riceSBEIIR.seq 1    CTCGAGTCTN  NNNNNNNNNN  NNNNNNNNNN  NNNNNNNNNN  NNNNNNNNNN  NNNNN
56   NNNNNNNNNN  NNNNNNNNNN  NNNNNNNNNN  NNNNNNNNNN  NNNNNNNNNN  NNNNN
111  NNNNNNNNNN  NNNNNNNNNN  NNNNNNNNNN  NNNNNNNNNN  NNNNNNNNNN  NNNNN
166  NNNNNNNNNN  NNNNNNNNNN  NNNNNNNNNN  NNNNNNNNNN  NNNNNNNNNN  NNNNN
221  NNNNNNNNNN  NNNNNNNNNN  NNNNNNNNNN  NNNNNNNNNN  NNNNNNNNNN  NNNNN
276  NNNNNNNNNN  NNNNNNNNNN  NNNNNNNNNN  NNNNNNNNNN  NNNNNNNNNN  NNNNN
331  NNNNNNNNNN  NNNNNNNNNN  NNNNNNNNNN  NNNNNNNNNN  NNNNNNNNNN  NNNNN
386  NNNNNNNNNN  NNNNNNNNNN  NNNNNNNNNN  NNNNNNNNNN  NNNNNNNNNN  NNNNN
441  NNNNNNNNNN  NNNNNNNNNN  NNNNNNNNNN  NNNNNNNNNN  NNNNNNNNNN  NNNNN
496  NNNNNNNNNN  NNNNNNNAGC  ATCAGATTTC  TTGATCAGGA  GCAACTGTTG  GTGCC
551  CTTGTAAACT  AGTGAATTC
```

Figure 8

SEQUENCE LISTING

<160> NUMBER OF SEQ ID NOS: 3

<210> SEQ ID NO 1
<211> LENGTH: 2739
<212> TYPE: DNA
<213> ORGANISM: Oryza sativa
<220> FEATURE:
<221> NAME/KEY: misc_feature
<223> OTHER INFORMATION: sbeI cDNA

<400> SEQUENCE: 1

```
gccaccgaca tccgccgcaa tgctgtgtct cacctcctct tcctcctccg cgcccgctcc      60
gctccttccc tctctcgctg atcgaccgag cccgggaatc gcgggcgggg gtggcaatgt     120
tcgcctgagc gtggtttctt cgccgcgccg gtcgtggcct ggaaaggtca agaccaattt     180
ctcagttcct gcgactgcgc gaaaaaacaa accatggtg  actgttgtgg aggaggtcga     240
ccaccttcct atatatgatc tggaccctaa gttggaggaa ttcaaggatc acttcaacta     300
taggataaaa agatacctcg accagaaatg cctgattgaa aaacatgagg ggggccttga     360
agaattttct aaaggctatt tgaagtttgg gattaataca gttgatggtg ccacaatata     420
tcgtgaatgg gcgcctgctg cacaagaagc acagctcatt ggtgagttca ataactggaa     480
tggtgcaaaa cacaagatgg agaaggataa atttggcatt tggtcaatca agatttcaca     540
tgtcaatggg aagcctgcca tccctcacaa ttccaaggtt aaatttcgct ttaggcatgg     600
gggtggagca tgggttgatc gtattcccgc atggattcgt tatgcaactt ttgatgcctc     660
taaatttgga gctccatatg atggtgtaca ctgggatcct ccagcctgtg aaaggtacgt     720
gtttaagcat cctcgacctc caaaacctga tgctccacgc atctatgagg ctcatgtggg     780
gatgagtggt gaagagccag aagtaagcac atacagaaga tttgcagaca atgtgttacc     840
acgcatacgg gcaaataact acaacacagt tcagttaatg gcaatcatgg aacattccta     900
ctatgcttct tttgggtatc acgtgacaaa tttttttcgca gtcagcagca gatcaggaac     960
accagaggat ctgaaatatc ttgttgacaa ggcacatagt ttaggattac gagttctgat    1020
ggatgttgtc catagccatg cgagtaataa tgtgaccgat ggtctaaatg ctatgacgt     1080
tggacaaaac actcatgagt cttattttca tacaggagat aggggctacc ataaactctg    1140
ggatagtcgt ctgttcaact atgccaattg ggaggtctta agatttcttc tttctaatttt    1200
gagatattgg atggacgaat tcatgtttga tggcttccga tttgatgggg ttacatcaat    1260
gctataccat caccatggta tcaataaggg atttactgga aactacaagg agtatttcag    1320
tttggatacc gatgtggatg caattgttta catgatgctc gcaaaccatt taatgcataa    1380
actcttgccg gaagcaacta tgttgctgaa agatgtttcg ggcatgccag tgctttgtcg    1440
gccagttgat gaaggtggag tagggtttga cttccgcctg gcaatggcca ttcctgatag    1500
atggattgac tacctgaaga caaagagga  ccgcaaatgg tcaatgagtg aaatagtgca    1560
aactttgact aacaggagat atacagaaaa atgcattgcc tatgccgaga ccatgatca     1620
gtccattgtt ggtgacaaga ctatagcatt tctcttgatg acaaggaaa tgtacactgg    1680
catgtcagac ttgcagcctg cttcacctac catcaaccgt ggcattgcac tccaaaagat    1740
gattcacttc attacgatgg cccttggagg tgatggctac ttaaatttta tgggcaatga    1800
gtttggccat ccagaatgga ttgactttcc aagagaaggc aacaactgga gctatgataa    1860
atgcagacgt cagtggagcc ttgtcgacac tgatcacctt cgatacaagt atatgaatgc    1920
atttgatcaa gcaatgaatg cactcgagga ggaattttcc ttcctgtcat catcaaagca    1980
```

| | |
|---|---|
| gattgttagc gacatgaacg agaaagataa ggttattgtc tttgaacgtg gagatttggt | 2040 |
| ttttgttttc aatttcatc ccaacaaaac ttacaagggt tacaaagtcg gatgtgactt | 2100 |
| gcccgggaag tacagagtag ctctggactc tgatgctttg gtctttggtg gccatggaag | 2160 |
| agttggccat gatgtggatc acttcacgtc tcccgaggga atgccaggag taccagaaac | 2220 |
| aaatttcaac aaccgcccta actcattcaa agtccttcc ccgccccgta cctgtgtggc | 2280 |
| ttactatcgc gttgatgaag atcgtgaaga gctcaggagg ggtggagcag ttgcttctgg | 2340 |
| aaagattgtt acagagtata tcgatgttga agcaacaagt ggggagacta tctctggtgg | 2400 |
| ctggaagggc tccgagaagg acgattgtgg caagaaaggg atgaagtttg tgtttcggtc | 2460 |
| ttctgacgaa gactgcaaat gaagcatcag atttcttgat caggagcaac tgttggtgcc | 2520 |
| cttgtaatct ggagatcctg gcttgccttg gacttggttg tggttcttta gcagttgcta | 2580 |
| tgtacctatc tatgatatga actttatgta tagttcgcct taaagaaaga ataagcagtg | 2640 |
| atgatgtggc cttaaacctg agctgcacaa gcctaatgta aaaataaagt ttcaggcttt | 2700 |
| catccagaat aaaacagctg ttcatttacc atctcaaaa | 2739 |

<210> SEQ ID NO 2
<211> LENGTH: 3015
<212> TYPE: DNA
<213> ORGANISM: Oryza sativa
<220> FEATURE:
<221> NAME/KEY: misc_feature
<223> OTHER INFORMATION: sbeIIa cDNA

<400> SEQUENCE: 2

| | |
|---|---|
| cttgactccc ccactcctc cctcgtgctg ctcctcctcg tcgctcggct cgaggcgcgg | 60 |
| catttgcggc gggagggatc tgcgcgcgag tgcgtgcggg caggcggcgg gggagcacgc | 120 |
| accgggggat ggcgtcgttc gcggtgtccg gcgcgaggct cggggtcgtg cggcgggggg | 180 |
| gcggcggcgg cggcggggt ggcccggcgg cgcgatccgg cggggtggac ttgccgtcgg | 240 |
| tgctcttcag gaggaaggac tccttctcac gtggcgttgt gagctgcgcg ggtgctcctg | 300 |
| ggaaggtgct ggtgcctggc ggtgggagcg acgacttgct gtcctctgcg gaaccagacg | 360 |
| tggaaactca agagcaacct gaagaatctc agataccaga tgataataaa gtaaaaccttt | 420 |
| ttgaggagga ggaagagatt ccagcagtgg cagaagcaag cataaaggtt gtggctgaag | 480 |
| acaaacttga atcttcagaa gtgattcaag acattgagga aaatgtgact gagggtgtga | 540 |
| tcaaagatgc tgatgaacca actgtggagg ataaaccacg agttatccca ccaccaggag | 600 |
| atgggcagaa gatataccaa attgacccaa tgctggaagg atttcggaac catcttgact | 660 |
| accgatacag tgaatacaag agaatgcgtg cagctattga ccaacatgaa ggtggcttgg | 720 |
| atgcattttc tcgtggttac gaaaagcttg gattcacccg cagcgctgaa ggcattacct | 780 |
| accgagaatg ggcacctgga gcacagtctg cagcattagt aggtgacttc aacaattgga | 840 |
| acccaaatgc agatactatg accagaaatg agtatggtgt ttgggagatt ccctgccta | 900 |
| acaatgctga tggatcccct gctattcctc atggctcacg tgtaaagatt cggatggata | 960 |
| caccatctgg cgtaaaggat tcaattcctg cctggattaa gtttgctgtg caggctccag | 1020 |
| gtgaaatacc gtacaacggt atatattatg atccacctga agaagaaaaa tatgtattcc | 1080 |
| aacatcctca acctaaacga ccaaattcgc tgcggatata tgaatcacat attggaatga | 1140 |
| gtagcccgga accgaagata aacacatatg ctaattttag ggatgaggtg ctaccaagaa | 1200 |
| ttaaaaagct tgggtacaat gctgtacaga taatggcaat ccaggagcac tcttattacg | 1260 |

```
caagctttgg gtatcatgtt actaacttct ttgcgccaag tagccgtttc ggaaccccag    1320
aagacttgaa atctctgatt gataaagctc acgagcttgg tttgcttgta cttatggata    1380
ttgttcacag tcatgcatca aacaataccc tggatggttt gaatggtttt gatggtactg    1440
atacacatta cttccatggt ggaccacggg gtcatcactg gatgtgggat tctcgcctgt    1500
tcaactatgg gagttgggaa gttttaagat atttactgtc gaatgcaagg tggtggcttg    1560
aagaatacaa gtttgatggg tttcgatttg atggggtgac ctccatgatg tatactcatc    1620
atggtttaca ggtggcattt actggcaact atggcgaata ttttggattt gctactgatg    1680
ttgatgcagt agtttacttg atgctggtga acgatctaat tcatgggctt tatcctgagg    1740
ctgtagccat tggtgaagat gtcagcggga tgcccacatt ttgtattcct gttcaagatg    1800
gtggtgttgg ttttgactat cgtttgcata tggctgtacc ggacaaatgg atcgaactcc    1860
tcaagcaaag tgacgaatat tggaaaatgg gtgatatcgt gcacacccta acgaatagaa    1920
ggtggtcaga gaagtgtgtt acttatgcag aaagtcatga ccaagcacta gttggtgaca    1980
agactattgc attctggttg atggataagg atatgtatga ttttatggct ctagacagac    2040
cttcaacacc tcgcattgat cgtgggatag cattacataa aatgattagg cttgtcacca    2100
tgggcttagg aggcgaaggc tatcttaatt tcatgggaaa tgagtttggg catcctgaat    2160
ggatagattt cccaagaggc ccgcaaagtc ttccaaatgg ctcggtcctc ccaggaaaca    2220
actacagttt tgataaatgc cgtcgtagat ttgaccttgg agatgcagat tatcttagat    2280
atcatggtat gcaagagttt gatcaggcca tgcagcatct tgaggaaaaa tatggattca    2340
tgacatctga gcaccagtat atatcgcgca aacacgagga ggataaggtg atcatcttcg    2400
agagaggaga tttggtattc gtgttcaact tccactggag taatagctat tttgactatc    2460
gcgtcggttg tttaaagcct ggaaagtaca agattgtgtt ggactcagac gatggcctct    2520
ttggtggatt cagtcggctt gatcatgatg ctgagtactt cactgctgac tggccgcatg    2580
acaacagacc atgttcattc tcggtgtaca ccccaagcag aaccgccgtc gtgtatgcac    2640
ttacagagga ctaatgatca gctctgatca ttgggggaac aactcaaggg agttggtggt    2700
aatgacgccg gaatacaact caagtgaaag gtgaaaagaa aggctgccct gacgatgtga    2760
tttgaggggc ttgtgtttca tcgccaatgc aggaagatg aggtagaaaa gcctactgat    2820
gagctcctgt tttcgagtga ctcgtgaagg aaatagacca gggtgaacgg cttttttcag    2880
agctatacca aacccatcct atgttgcgca ttcgctgtag ttttgtacat aacgatatcg    2940
gttggcattt gtatgtttat gaataatctg ttcgacagaa atgtttttct ccttgtattt    3000
agtgctcaaa aaaaa                                                     3015
```

<210> SEQ ID NO 3
<211> LENGTH: 2918
<212> TYPE: DNA
<213> ORGANISM: Oryza sativa
<220> FEATURE:
<221> NAME/KEY: misc_feature
<223> OTHER INFORMATION: sbeIIb cDNA

<400> SEQUENCE: 3

```
cggcgcacac ccacacaccg accaccaggc agcgcctcct cgctttggct ctcgcgtgag      60
gagggtttag gtggaagcag agcgcggggg ttgccggggg atccgatccg gctgcggtgc     120
gggcgagatg gcggcgccgg cgtctgcggt tcccggagc gcggcggggc tacgggcggg     180
ggccgtgcgg ttccccgtgc cagccggggc ccggagctgg cgtgcggcgg cggagctccc     240
```

```
gacgtcgcgg tcgctgctct ccggccggag attccccggt gccgttcgcg tggggggttc     300
cggggggcgc gtggccgtgc gcgcggcggg cgcgtcaggg gaggtgatga tccccgaggg     360
cgagagcgac gggatgccgg tttcagcagg ttcagacgat ctgcagttgc cagccttaga     420
tgatgaatta agcacggagg ttggagctga agttgagatt gagtcatctg gagcaagtga     480
cgttgaaggc gtgaagagag tggttgaaga attagctgct gagcagaaac cacgagttgt     540
cccaccaaca ggagatgggc aaaaaatatt ccagatggac tctatgctta atggctataa     600
gtaccatctt gaatatcgat atagcctata taggagactg cgttcagaca ttgatcagta     660
tgaaggagga ctggaaacat tttctcgcgg ttatgagaag tttggattta atcacagtgc     720
tgaaggtgtc acttatcgag aatgggctcc cggggcacat tctgcagcat tagtaggtga     780
cttcaacaat tggaatccaa atgcagaccg catgagcaaa aatgagtttg gtgtttggga     840 gattttctg cctaacaatg ctgatggctc atctcctatt ccacatggct cacgtgtaaa      900
ggtgcgaatg gaaactccat ctggtataaa ggattctatt cctgcctgga tcaagtactc     960
tgtgcaggcc gcaggagaaa tcccatacaa tggaatatat tatgatcctc ctgaagagga    1020
gaagtacata ttcaagcatc ctcaacctaa aagaccaaag tcattgcgga tatacgaaac    1080
tcatgttgga atgagtagca cggagccaaa gatcaacacg tatgcaaact tagggatga    1140 ggtgcttcca agaatcaaaa agcttggata caatgcagtg caaataatgg caattcaaga    1200
gcatgcatat tatggaagct ttgggtacca tgtcaccaat ttctttgcac caagtagtcg    1260
tttcgggacc ccagaagatt taaagtcatt gattgataaa gctcatgagc ttggtttagt    1320
tgtgctcatg gatgttgttc acagccatgc gtcaaataat accctagatg ggttgaacgg    1380
ttttgatggt acagatacgc attactttca tagtggttca cgcggccatc attggatgtg    1440
ggattctcgc cttttcaact atgggaattg gaagttccta agatttctac tatccaatgc    1500
aagatggtgg ctcgaggagt ataagtttga tggtttcaga tttgacggtg taacctcaat    1560
gatgtacact catcatggat tacaagtagc atttacgggg aactacagtg aatactttgg    1620
atttgccact gatgctgatg cagtagttta cttgatgctg gtaaatgatt taattcatgg    1680
actttatcct gaggccataa ccatcggtga agatgtcagt ggaatgccta catttgccct    1740
tcctgttcaa gatggtgggg ttggttttga ttatcgcctt catatggctg ttcctgacaa    1800
atggattgaa ctcctcaagc aaagtgatga atccttggaag atgggtgata ttgtgcacac    1860
actgactaac agaaggtggt cagagaagtg tgttacttat gctgaaagtc atgatcaagc    1920
actagttggt gacaaaacta ttgcattctg gttgatggac aaggatatgt atgattttat    1980
ggctctggac agaccggcaa cacctagcat tgatcgtgga atagcattgc ataaaatgat    2040
tagacttatc acaatggggt taggaggaga aggctatctt aactttatgg gaaatgagtt    2100
cggacatcct gaatggattg attttccaag agctccacaa gtacttccaa atggtaaatt    2160
catcccaggg aataacaaca gttatgataa atgccgtcga agatttgacc tgggtgatgc    2220
ggactatctt aggtatcgtg gcatgctaga gtttgaccgc gcgatgcagt ctctcgagga    2280
aaaatatggg ttcatgacat cagaccacca gtacatatct cgaaagcatg aagaggataa    2340
gatgattata tttgagaagg gagatctggt atttgtgttc aacttccatt ggagtaacag    2400
ctattttgac taccgtgttg gttgtttaaa gccagggaaa tataaggtgg tcttggactc    2460
agatgctgga ctcttggtg gatttggcag gatccatcac actgcagagc acttcactgc    2520
cgattgttca catgacaaca ggccctactc gttctcagtt tattctccta gcagaacctg    2580
cgttgtctat gctccagcgg aatgagaaca ccaagaggca gcatgcaagt gtgtgcggct    2640
```

```
gctagtgcga aggagcaaga aaaactagtt gccagcaatc tgtgaacggc tttcctaggt    2700
tctgcttcga tgaatgccgg atagactaga cagcttgctt ttgtgctttg cgctcccaat    2760
ttgtagtttt agtttgtgag ggaaagaaac gtttatttgt aattatctat ggctgtcgaa    2820
cggcgacgaa accatgaacc ccgtatattt gttggtaccg ttcgaactgc cagttataca    2880
tagttctgca cttctgtaca tcttgtgatg cttgaatc                            2918
```

RICE AND PRODUCTS THEREOF HAVING STARCH WITH AN INCREASED PROPORTION OF AMYLOSE

This application is a continuation of U.S. Ser. No. 12/806,167, filed Aug. 6, 2010 now U.S. Pat. No. 8,188,336, a divisional of U.S. Ser. No. 10/577,564, filed Apr. 27, 2006, now U.S. Pat. No. 7,790,955, issued Sep. 7, 2010 a §371 national stage of PCT International Application No. PCT/AU2004/001517, filed Oct. 27, 2004, on behalf of Commonwealth Scientific And Industrial Research Organisation, claiming priority of U.S. Provisional Application No. 60/515,102, filed Oct. 27, 2003, the contents of each of which are hereby incorporated by reference.

FIELD OF THE INVENTION

This invention relates to a rice plant having kernel starch with a high relative amylose content. The invention also relates to rice with a reduced starch branching enzyme IIa (SBEIIa) activity in the endosperm. The invention also relates to grain and starch and food and non-food products obtained therefrom.

BACKGROUND OF THE INVENTION

Cereal starch comprises two types of molecule, amylose and amylopectin. Amylose is an essentially linear molecule composed of α-1,4 linked glucosidic units, while amylopectin is highly branched with α-1,6 glucosidic bonds linking linear eluting.

The synthesis of starch in the endosperm of higher plants is carried out by a suite of enzymes that catalyse four key steps. Firstly, ADP-glucose pyrophosphorylase (ADGP) activates the monomer precursor of starch through the synthesis of ADP-glucose from G-1-P and ATP. Secondly, the activated glucosyl donor, ADP-glucose, is transferred to the non-reducing end of pre-existing α-1,4 linked chains by starch synthases. Thirdly, starch branching enzymes (SBE) introduce branch points through the cleavage of a region of α-1,4 linked glucan followed by transfer of the cleaved chain to an acceptor chain, forming a new α-1,6 linkage. SBEs are the only enzymes that can introduce the α-1,6 linkages into α-polyglucans and therefore play an essential role in the formation of amylopectin. Finally, starch debranching enzymes remove some of the branch linkages, although the mechanism through which they act is unresolved (Myers et al., 2000). While it is clear that at least these four activities are required for normal starch granule synthesis in higher plants, multiple isoforms of each of the four activities are found in the endosperm of higher plants and specific roles have been proposed for individual isoforms on the basis of mutational analysis (Wang et al, 1998a, Buleon et al., 1998) or through the modification of gene expression levels using transgenic approaches (Abel et al., 1996, Jobling et al., 1999, Schwall et al., 2000). However, the precise contributions of each isoform of each activity to starch biosynthesis are still not known, and it is not known whether these contributions differ markedly between species.

In the cereal endosperm, two isoforms of ADP-glucose pyrophosphorylase are present, one form within the amyloplast, and one form in the cytoplasm (Denyer et al., 1996, Thorbjornsen et 1996). Each form is composed of two subunit types. The shrunken (sh2) and brittle (bt2) mutants in maize represent lesions in large and small subunits respectively (Giroux and Hannah, 1994). Four classes of starch synthase are found in the cereal endosperm, an isoform exclusively localised within the starch granule, granule-bound starch synthase (GBSS), two form a that are partitioned between the granule and the soluble fraction (SSI, Li et al., 1999a, SSII, Li et al., 1999b) and a fourth form that is entirely located in the soluble fraction, SSIII (Cao et al., 2000, Li et al., 1999b, Li et 2000). GBSS has been shown to be essential for amylase synthesis (Shure et al., 1983), and mutations in SSII and SSIII have been shown to alter amylopectin structure (Gao et 1998, Craig et al., 1998). The rice GBSS (waxy) gene sequence has been described (Wang et al., 1990), and expression inhibited by antisense methods (Terada et al., 2000). The waxy gene is expressed in endosperm and pollen but not in other rice organs (Hirano and Sano, 2000).

Two main classes of SBEs are known in plants, SBEI and SBEII. SBEII can further be categorized into two types in cereals, SBEIIa and SBEIIb (Boyar and Preiss, 1978; Gao at al., 1996; Fisher et al., 1996; Hedman and Boyer, 1982; Mizuno et al., 1992; Sun et al., 1997; Sun et al, 1998). Additional forms of SBEs are also reported in some cereals, the putative 149 kDa SBEI from wheat (Bags et al., 2000) and the 50/51 kDa SBE from barley (Sun et al., 1996). Cenozoic and cDNA sequences have been characterized for rice (Nakamura and Yamanouchi, 1992; Mizuno et al, 1992; Mizuno et al, 1993; Mizuno et al, 2001), maize (Baba et al., 1991; Fisher et al., 1993; Geo et al., 1997) wheat (Repellin et al., 1997; Nair et al., 1997; Rahman et al., 1997) and other cereals. Sequence alignment reveals a high degree of sequence similarity at both the nucleotide and amino acid levels and allows the grouping into the SBEI, SBEIIa and SBEIIb classes. SBEIIa and SBEIIb generally exhibit around 80% sequence identity to each other, particularly in the central regions of the genes.

SBEIIb, SBEIIb and SBEI may also be distinguished by their expression patterns, both temporal and spatial, in endosperm and in other tissues. SBEI is expressed from mid-endosperm development onwards in wheat and maize (Morell et al., 1997). In contrast, SBEIIa and SBEIIb are expressed from an early stage of endosperm development. In maize, SBEIIb is the predominant form in the endosperm whereas SBEIIa is present at high expression levels in the leaf (Geo et al., 1997). In rice, SBEIIa and SBEIIb are found in the endosperm in approximately equal amounts (Yamanonchi and Nakamura, 1992). However, there were differences in timing and tissues of expression. SBEIIa is expressed at an earlier stage of seed development, being detected at 3 days after flowering (DAF), and was expressed in leaves, while SBEIIb was not detectable at 3 DAF and was most abundant in developing seeds at 7.10 DAF and was not expressed in leaves (Mizuno et al., 2001). In wheat endosperm, SBEI (Morell et al., 1997) is found exclusively in the soluble fraction, while SBEIIa and SBEIIb are found in both soluble and starch-granule associated fractions (Rahman et al., 1995).

Two types of debranching enzymes am present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (lames et al., 1995, Kubo et al., 1999) however the causal mutation maps to the same location as the isoamylase-type debranching enzyme gene. In rice, antisense inhibition of isoamylase altered the structure of amylopectin and starch properties (Fujita et al., 2003), showing that isoamylase was required for amylopectin biosynthesis.

Representative starch branching enzyme genes that have been cloned from cereals are listed in Table 1.

TABLE 1

Starch branching enzyme genes characterized from cereals including rice.

| Species | SBE isoform | Type of clone | Accession No. | Reference |
|---|---|---|---|---|
| Rice | SBEI | cDNA | D10752 | Nakamura and Yamanouchi, 1992 |
|  | SBEI | genomic | D10838 | Kawasaki et al., 1993 |
|  | RBE3 | cDNA | D16201 | Mizuno et al., 1993 |
|  | RBE4 | cDNA | AB023498 | Mizuno et al., 2001 |
| Maize | SBEI | cDNA | U17891 | Fisher et al., 1995 |
|  |  | genomic | AF072724 | Kim et al., 1998a |
|  | SBEIIb | cDNA | L08065 | Fisher et al., 1993 |
|  |  | genomic | AF072725 | Kim et al., 1998 |
|  | SBEIIa | cDNA | U65948 | Gao et al., 1997 |
| Wheat | SBEII | cDNA | Y11282 | Nair et al., 1997 |
|  | SBEI | cDNA and genomic | AJ237897 (SBEI gene) | Baga et al., 1999 |
|  |  |  | AF002821 (SBEI pseudogene | Rahman et al., 1997, |
|  |  |  | AF076680 (SBEI gene) |  |
|  |  |  | AF076679 (SBEI cDNA) | Rahman et al., 1999 |
|  | SBEI | cDNA | Y12320 | Repellin et al., 1997 |
|  | SBEIIa | cDNA and genomic | AF338432 (cDNA) AF338431 (gene) | Rahman et al., 2001 |
|  | SBEIIb | cDNA and genomic |  | WO 01/62934 |
|  | SBEIIb | cDNA |  | WO 00/15810 |
| Barley | SBEIIa and SBEIIb | cDNA and genomic | AF064563 (SBEIIb gene) AF064561 (SBEIIb cDNA) AF064562 (SBEIIa gene) AF064560 (SBEIIa cDNA) | Sun et al., 1998 |

In maize and rice, high amylose phenotypes have been shown to result from lesions in the SBEIIb gene, also known as the amylase extender (as) gene (Boyer and Preiss, 1981, Mizuno et al., 1993; Nishi et al., 2001). In these SBEIIb mutants, endosperm starch grains showed an abnormal morphology, amylose content was significantly elevated, the branch frequency of the residual amylopectin was reduced and the proportion of short chains (<DP17, especially DP8-12) was lower. Moreover, the gelatinisation temperature of the starch was increased. In addition, there was a significant pool of material that was defined as "intermediate" between amylose and amylopectin (Boyer et al., 1980, Takeda, et al., 1993b). In rice, inactivation of SBEIIb led to an amylose content of about 25% compared to wild-type rice which has about 18% amylose (Nishi et al., 2001).

In contrast, maize plants mutant in the SBEIIa gene due a mutator (Mu) insertional element and consequently lacking in SBEIIa protein expression were indistinguishable from wild-type plants in the branching of endosperm starch (Blauth et al., 2001), although they were altered in leaf starch. Similarly, rice plants deficient in SBEIIa activity exhibited no significant change in the amylopectin chain profile in endosperm (Nakamura 2002). In both maize and rice, the SBEIIa and SBEIIb genes are not linked in the genome.

Very high amylose varieties of maize have been known for some time. LAPS (low amylopectin starch) maize which contains very high amylase content (>90%) was achieved by a considerable reduction in the SBEI activity together with an almost complete inactivation of SBEII activity (Sidebottom et al., 1998).

In potato, down regulation of the main SBE in tubers (SBE B, equivalent to SBEI) by antisense methods resulted in some novel starch characteristics but did not alter the amylose content (Safford et al., 1998). Antisense inhibition of the less abundant form of SBE (SBE A, analogous to SBEII in cereals) resulted in a moderate increase in amylose content to 38% (Jobling et al., 1999). However, the down regulation of both SBEII and SBEI gave much greater increases in the relative amylose content, to 60-89%, than the down-regulation of SBEII alone (Schwall et al., 2000).

In wheat, a mutant entirely lacking the SGP-1 (SSII) protein was altered in amylopectin structure and had deformed starch granules and an elevated amylose content to about 30-37% of the starch, which was an increase of about 8% over the wild-type level (Yamamori et al., 2000). Amylose was measured by calorimetric measurement, amperometric titration (both for iodine binding) and a concanavalin A method. Starch from the SSII null mutant exhibited a decreased gelatinisation temperature compared to starch from an equivalent, non-mutant plant. Starch content of the grain was reduced from 60% in the wild-type to below 50%.

In maize, the dull1 mutation causes decreased starch content and increased amylose levels in endosperm, with the extent of the change depended on the genetic background, and increased degree of branching in the remaining amylopectin (Shannon and Garwood, 1984). The gene corresponding to the mutation was identified and isolated by a transposon-tagging strategy using the transposon mutator (Mu) and shown to encode the enzyme designated starch synthase II (SSII) (Gao et al., 1998). The enzyme is now recognized as a member of the SSIII family in cereals (Li et al., 2003). Mutant endosperm had reduced levels of SBEIIa activity associated with the dull1 mutation. It is not known if these findings are relevant to other cereals, for example rice.

Lines of barley having an elevated proportion of amylase in grain starch have been identified. These include High Amylose Glacier (AC38) which has a relative amylose content of about 45%, and chemically induced mutations in the SSIIa gene of barley which raised levels of amylose in kernel starch to about 65-70% (WO 0237955 A1; Morel et al., 2003). The starch showed reduced gelatinisation temperatures.

Rice (*Oryza sativa* L.) is the most important cereal crop in the developing world and is grown widely, particularly in Asia which produces about 90% of the world total.

Starch is widely used in the food, paper and chemical industries. The physical structure of starch can have an important impact on the nutritional and handling properties of starch for food or non-food or industrial products. Certain characteristics can be taken as an indication of starch structure including the distillation of amylopectin chain length, the degree and type of crystallinity, and properties such as gelatinisation temperature, viscosity and swelling volume. Changes in amylopectin chain length may be an indicator of altered crystallinity, gelatinisation or retrogradation of the amylopectin.

Starch composition, in particular the form called resistant starch which may be associated with high amylose content, has important implications for bowel health, in particular health of the large bowel. Accordingly, high amylose starches have been developed in certain grains such as maize and barley for use in foods as a means of promoting bowel health. The beneficial effects of resistant starch result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally if resistant starches or other dietary fiber is not provided the colon is metabolically relatively inactive.

Whilst chemically or otherwise modified starches can be utilised in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

Therefore, rice having starch with a proportion of amylose greater than 40% is unknown. Although high amylose maize and barley varieties are known, vex), high amylose rice is preferred for rice growing regions. Starch from such rice is relatively resistant to digestion and therefore very high amylose rice is expected to bring an important health benefit to a substantial portion of the world population.

General

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of my other integer or step or group of integers or steps. The present invention is not to be limited in scope by the specific embodiments described herein, which are intended for the purposes of exemplification only. Functionally-equivalent products, compositions and methods are clearly within the scope of the invention, as described herein.

Bibliographic details of the publications referred to by author in this specification are collected at the end of the description. The references mentioned herein are hereby incorporated by reference in their entirety. Reference herein to prior art, including any one or more prior art documents, is not to be taken as an acknowledgment, or suggestion, that said prior art is common general knowledge in Australia or forms a part of the common general knowledge in Australia.

As used herein, the term "derived from" shall be taken to indicate that a particular integer or group of integers has originated from the species specified, but has not necessarily been obtained directly from the specified source.

The designation of nucleotide residues referred to herein are those recommended by the IUPAC-IUB Biochemical Nomenclature Commission, wherein A represents Adenine, C represents Cytosine, G represents Guanine, T represents Thymidine.

SUMMARY OF THE INVENTION in a first aspect the invention might be said to reside in grain obtained from a rice plant, comprising starch, wherein the proportion of amylose in the starch of the grain is at least 40%. The grain preferably has reduced activities or levels of SBEIIa and SBEIIb, and in one form this might be achieved by two or more genetic variations, wherein one genetic variation is selected from the group consisting of a) a mutation of an SBEIIa gene which inhibits SBEIIa expression and/or activity, and b) an introduced nucleic acid which inhibits SEEM expression and/or activity, and wherein a second genetic variation is selected from the group consisting of a) a mutation of an SBEIIb gene which inhibits SBEIIb expression and/or activity, and b) an introduced nucleic acid which inhibits SBEIIb expression and/or activity.

The grain of in one form comprises a transgene which transgene may encode an antisense, co-suppression, ribozyme or duplex RNA molecule. Alternatively the grain may be non-transgenic the inhibition results from chromosomal mutation or rearrangement. The grain may comprise a null mutation of the SBEIIa or SBEIIb gene.

The grain of claim of the first aspect may comprise reduced levels of SEEM and SBEIIb proteins and/or activities. In a specific form the grain may further comprising a reduced level of SBEI protein and/or activity or may additionally or alternatively also comprise an altered level of a protein and/or enzyme activity selected from the group consisting of ADP glucose pyrophosphorylase, GBSS, SSI, SSII, SSIII, a debranching enzyme of an isoamylase type and a debranching enzyme of a pullulanase type. In a specific alternative form the grain comprises an altered level of GBSS protein and/or enzyme activity. In a further optional form the grain is of an Indica variety or which comprises a $Wx^a$ allele.

The proportion of amylose in the starch of the grain in a preferable than is at least 50%.

The grain is preferably non-shrunken and in a specific form has in a brown rice form an average weight of at least about 25 mg and preferably also a starch content that is at least 90% of the starch content of equivalent, but unaltered, grain. Preferably also at least 50% of starch granules within the grain appear non-birefringent when observed under polarized light.

The invention also encompasses in a second aspect a rice plant capable of producing the grain of the first aspect of the invention.

Third and fourth aspects of the invention relates to starch and starch granules extracted from the grain of the first aspect of the invention.

In a fifth aspect the invention relates to a product comprising flour or starch produced from the grain of the first aspect of the invention. The product may include a blend of the flour or starch with flour or starch from another source. The product may be a food or a non-food product.

A sixth aspect of the invention encompasses a composition comprising the starch of the third aspect and another food ingredient or water.

A seventh aspect of the invention might be said to reside in a method of producing a rice plant capable of producing grain, the grain having starch comprising at least 40% amylose, comprising the steps of a) introducing a genetic variation into a parent rice plant or seed; and b) identifying a progeny plant of the parent rice plant or seed, wherein the starch of grain of the progeny plant comprises at least 40% amylose. Preferably the genetic variation leads to a reduction oldie levels of SBEIIa and SBEIIb proteins and/or activities in the endosperm of the rice plant.

The progeny rice plant of the method preferably comprises two or more genetic variations, wherein one genetic variation is selected from the group consisting of a) a mutation of an SBEIIa gene which inhibits SBEIIa expression and/or activity, and b) an introduced nucleic acid which inhibits SBEIIa expression and/or activity, and wherein a second genetic variation is selected from the group consisting of c) a mutation of an SBEIIb gene which inhibits SBEIIb expression and/or activity, and d) an introduced nucleic acid which inhibits SBEIIb expression and/or activity.

The step of introducing the genetic variation may comprise introducing an exogenous nucleic acid. The exogenous nucleic acid may be introduced into a rice cell which is then regenerated into a rice plant. The exogenous nucleic acid preferably encodes an inhibitor of SBEIIa and/or SBEIIb expression and/or activity, and the inhibitor may an antisense, co-suppression, ribozyme or duplex RNA molecule.

Alternatively the step of introducing the genetic variation may comprise mutagenesis of the parent rice pleat or seed with a chemical agent or radiation.

The progeny rice plant may comprise a null mutation in SBEIIa and/or SBEIIb.

The step of introducing a genetic variation may additionally leads to a reduction in the level of SBEI protein and/or activity.

The progeny plant may identified on the basis of the amylose level in the grain starch or on a reduction in the levels of SBEIIa and/or SBEIIb proteins and/or activities in the endosperm of the progeny plant.

The method may further comprise the introduction of a Wx$^a$ allele into the rice plant, which may be introduced by crossing.

An eighth aspect of the invention might be said to reside in a method of producing a rice plant having a reduced level of both SBEIIa and SBEIIb proteins and/or enzyme activities in the endosperm which comprises: a) mutagenising seed having a reduced level of SBEIIa protein and/or enzyme activity; or b) mutagenising seed having a reduced level of SBEIIb protein and/or enzyme activity; or c) crossing a plant baying a reduced level of SBEIIa protein and/or enzyme activity with a plant having a reduced level of SBEIIb protein and/or enzyme activity; and d) identifying a rice plant having reduced activity of both SBEIIa and SBEIIb proteins and/or enzyme activities in the endosperm.

The step of identifying the rice plant may comprise screwing a population of rice plants with a molecular marker that is linked to the SBEIIa gene or SBEIIb gene of rice, and identifying the plant on the basis of the presence or absence of a signal from the screening with the linked molecular marker.

The step of identifying the rice plant may comprises the step of screening seed from a population of rice plants with an antibody that binds the SBEIIa protein or SBEIIb protein of rice, and identifying the plant on the basis of the presence or absence of antibody binding.

The invention may also encompass a method of producing altered rice starch comprising the step of extracting starch from the grain of the first aspect of the invention.

The invention may additionally encompass the use of two or more exogenous nucleic acid molecules, at least one of which encodes an inhibitor of rice SBEIIa expression and/or activity and at least another of which encodes an inhibitor of rice SBEIIb expression and/or activity, to produce a rice plant which has reduced levels of SBEIIa and SBEIIb protein, and/or activities. The inhibitors may be selected from the group consisting of antisense molecules, co-suppression molecules, ribozymes, duplex RNA molecules end any combination of these.

The invention also encompasses an isolated nucleic acid molecule which encodes an inhibitor of rice SBEIIa and an inhibitor of rice SBEIIb, which may be the same or a different molecule. The isolated vector may be a vector. It will be understood that the invention encompasses a cell which comprises the isolated nucleic acid molecule, which preferably is a rice cell. The invention will also be understood to encompass a transgenic rice plant comprising the isolated nucleic acid molecule.

BRIEF DESCRIPTION OF THE DRAWINGS

FIG. 1. Sequence of a cDNA encoding rice Starch Branching Enzyme I gene (SBEI)—Genbank Accession No. D11082 (SEQ. ID. No 1).

FIG. 2. Sequence of a cDNA encoding rice Starch Branching Enzyme IIa gene (SBEIIa)—Genbank Accession No. AB023498 (SEQ ID No 2).

FIG. 3. Sequence of a cDNA encoding rice Starch Branching Enzyme IIb gene (SBEIIb)-Genbank Accession No. D16201 (SEQ ID NO 3).

FIG. 7. Comparison of the rice SBEIIa (SEQ ID NO 2) and rice SBEIIb (SEQ ID NO 3) cDNA sequences. The upper sequence (uppercase) is from SBEIIb, the lower sequence (lowercase) from SBEIIa. The 5' and 3' terminal sequences are not shown as they do not have sufficient degree of identity.

FIG. 8. BLAST output from Gene Silencing program using SBEIIa, SBEIIb and SBEI 3' sequences used in gene silencing constructs.

DETAILED DESCRIPTION OF THE INVENTION

Method of Producing a Rice Plant

Figure 4:
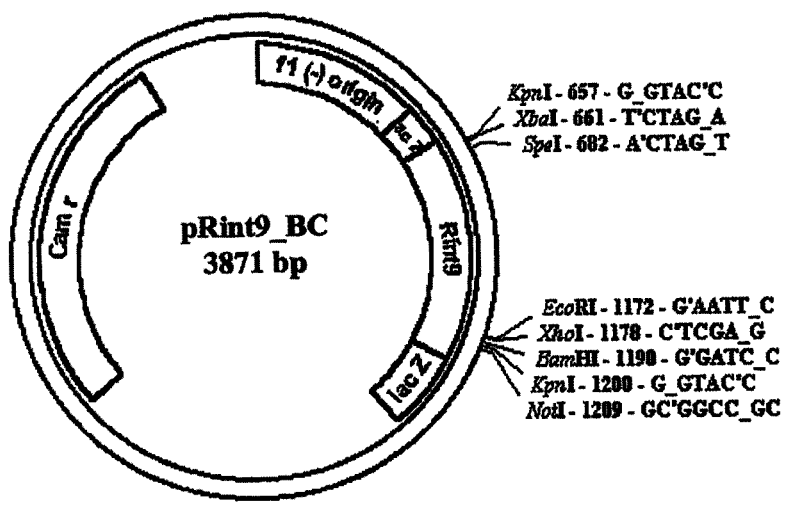
FIG. 4. Schematic diagram of plasmid pRint9_BC containing a 500 bp fragment of intron 9 of rice SBEI gene inserted into pBC SK−.

In an aspect, the invention provides a method of producing a rice plant having altered starch in its grain, in particular increasing the relative proportion of amylose in the starch to at least 40%. The proportion of amylose in the starch as defined herein is on a weight/weight (w/w) basis, i.e. the weight of amylose as a percentage of the weight of starch. The proportion of amylose in the starch is preferably at least 45%, 50%, 55% or 60% and even more preferably at least 65%, 70% or 75%. Ordinarily in rice, the proportion of amylose in starch ranges from about 0 to 35%. The method may include reducing the level of both starch branching enzyme IIa (SBEIIa) and starch branching enzyme IIb (SBEIIb) protein or enzyme activity in the endosperm of rice. The reduction in the proteins or activities may be by at least 40% or preferably by at least 60% compared to the corresponding levels of protein or activity in the endosperm of unmodified rice, more preferably by at least 75%, and even more preferably by at least 90% or 95%. One or both of the proteins may be undetectable in the rice endosperm. The method may comprise the alteration of the expression of the SBEIIa and SBEIIb genes of rice, or it may comprise the mutation of the SBEIIa and SBEIIb genes in rice, or a combination of these, whereby both the SBEIIa and SBEIIb activities in endosperm are reduced. The expression of either or both genes may be inhibited by the introduction of a nucleic acid, for example a transgene.

It would be readily apparent that the terms "increased", "decreased", "reduced" "altered" and the late as used herein are comparative terms that refer to a difference in the plants or products of the invention in comparison with corresponding wild-type plants or products, said wild type plants or products not being modified according to the invention.

Amylose is defined herein as including essentially linear molecules composed of α-1,4 linked glucosidic molecules and amylose long-chain amylopectin (sometimes referred to as "intermediate material", Takeda et al., 1993b; Fergason, 1994). Amylose content may be determined by any of the methods known in the art including size exclusion HPLC, for example in 90% (w/v) DMSO, concanavalin A methods (Megazyme Int, Ireland), or preferably by iodometric methods, for example as described in Example 1. The HPLC method may involve debranching of the starch (Batey and Curtin, 1996) or not involve debranching. From the grain weight and amylase contort, the amount of amylose deposited per grain can be calculated and compared for transgenic and control lines.

The method may comprise the step of determining the activities of SBEIIa and/or SBEIIb, preferably both, in rice endosperm. This may be done by measuring the levels of the protein, for example by immunodetection, or the levels of their corresponding mRNAs by methods well known in the art such as Northern blot hybridization analysis, slot-blot hybridization, RNAse protection assays, microarray analysis or reverse transcription polymerase chain reaction (RT-PCR). The method may further comprise the step of screening for a rice plant or grain having reduced SBEIIa and/or SBEIIb activities in its endosperm, or selecting or identifying such a plant or grain. The screening/selection step may be based on the reduced level of the SBEIIa and/or SBEIIb activity or protein, or it may be based on the phenotype of the grain of the rice plant such as an increased proportion of amylose or decreased proportion of amylopectin or a visual phenotype, for example shrunken grain.

SBE activity may be measured by enzyme assay, for example by the phosphorylase stimulation assay (Boyer and Preiss, 1978). This assay measures the stimulation by SBE of the incorporation of glucose 1-phosphate into methanol-insoluble polymer (α-D-glucan) by phosphorylase a. SBE activity can be measured by the iodine stain assay, which measures the decrease in the absorbency of a glucan-polyiodine complex resulting from branching of glucan polymers. SBE activity can also be assayed by the branch linkage assay which measures the generation of reducing ends from reduced amylose as substrate, following isoamylase digestion (Takeda et al., 1993a). Preferably, the activity is measured in the absence of SBEI activity. Isoforms of SBE show different substrate specificities, for example SBEI exhibits higher activity in branching amylose, while SBEIIa and SBEIIb show higher rates of branching with an amylopectin substrate. The iso forms may also be distinguished on the basis of the length of the glucan chain that is transferred. SBE protein may also be measured by using specific antibodies such as those described herein. In a preferred embodiment, SBEIIa and SBEIIb protein levels are measured by immunological methods such as Western blotting or ELISA assay using specific antibodies raised to polypeptide fragments corresponding to the N-terminal amino acid sequences of rice SBEIIa and SBEIIb. The SBEII activity may be measured during gain development in the developing endosperm, or alternatively in the mature grain where the protein is still present in equivalent, but unaltered, grain and can be assayed by immunological methods.

In a further aspect, the invention provides a method of altering, preferably reducing, the activity of a third starch biosynthesis enzyme in rice, in combination with the reduction in activity of SBEIIa and SBEIIb, such that the proportion of amylose in the starch of the grain is at least 40%. Preferably, SBEI activity in the endosperm is also reduced. Other starch biosynthesis enzymatic activities that may be altered in combination with SBEIIa and SBEIIb are: SSI, SSII, SSIII. Starch debranching enzymes may also be altered, for example the activity of isoamylase or pullulanase. The third starch biosynthetic enzyme activity may be increased or decreased, preferably decreased, by at least 40% compared to the activity in unmodified rice, preferably at least 60% or 80% and more preferably at least 90%.

In a further embodiment, the activities of starch biosynthesis enzymes may be altered in the plant in tissues other than endosperm, for example the activity of SBEI or SBEII, preferably SBEIIa, may be increased in leaves to compensate for some loss of activity caused by a genetic variation in the plant that leads to loss of SBEIIa activity in the endosperm. This is particularly preferred when the genetic variation leads to reduction in SBEIIa activity not only in the endosperm but also in other tissues, in particular the leaves. It would be appreciated that such compensation of activity in tissues other than the endosperm would, for example, be from an enzyme coding region under the control of a promoter that is not expressed in the endosperm. This may be a promoter from a photosynthesis-related gene such as rbcS. Alternatively, starch synthesis in the endosperm may be further improved by the overexpression of one or more starch biosynthetic enzymes in combination with a reduction in SBEII and SBEIIb activities in the endosperm. Genes encoding such enzymes may be from any of a variety of sources, for example from bacterial or other sources other than rice, and may be modified to alter the catalytic properties, for example alteration of the temperature dependence of the enzymes (WO94/09144).

The high amylose phenotype may be achieved by partial or full disruption to the expression of the SBEIIa and SBEIIb genes. The method of the invention may comprise the step of screening or identifying or selecting a rice plant or grain which has a null mutation in the SBEIIa and/or SBEIIb genes. A "null mutation" is defined herein as a mutation that leads to the lack of detectable protein or enzyme activity in the plant tissue of interest, preferably the endosperm. The screening/identifying step may therefore comprise a screen at the gene level, for example a screen for deletions in the gene encoding SBEIIa and/or SBEIIb, or at the level of expression of the gene of interest. The extent to which the genes are inhibited will in some degree determine the characteristics of the starch made in the rice grain. Screening for deletions may conveniently be carried out by PCR amplification methods using primers designed such that at least part of the amplification product spans at least part of the gene of interest. Any of a range of gel electrophoresis techniques carried out on the proteins extracted from the modified rice endosperm will reveal the nature and extent of modification to the SBEIIa and SBEIIb activities. Modification may occur as a reduction in SBEIIa and/or SEEM activities or complete abolition of enzyme activity within the endosperm. To carry out these tests, starch may be extracted from the rice endosperm and the proteins therein analyzed. Techniques well known in the art such as SDS-PAGE and immunoblotting may be carried out on the soluble and the starch granule fractions and identify the planet or grain where modifications have occurred to the SBEIIa and SBEIIb enzymes.

The method of the invention may comprise the introduction of a genetic variation into the rice plant or an ancestral rice plant or seed. The genetic variation may comprise a transgene, as described below, or may be introduced by mutagenesis, for example by chemical mutagenesis or by radiation.

Rice Plants

In a further aspect, the invention provides a rice plant capable of producing grain baying a proportion of amylose in the starch of at least 40%. A rice plant is defined herein as any plant of the species Oryza sativa L The rice plant may be of any of the three recognised races of O. sativa L, namely Japonica (or sinica), Indica and Javanica and is preferably an Indica variety. There are numerous cultivars or varieties in each race and all are included in the plants of the invention. Preferred cultivars are those grown in Australia including, for example, cultivars Amaroo, Ali Combo, Basmati, Bogan, Bombia, Doongara, Goolarah, Illabong, Jarrah, Koshihikari, Kyeema, Langi, Millin, Namage, Opus, Pelde. The proportion of amylose is preferably at least 45%, 50%, 55%, 60%, 65%, 70% or 75%. The rice plant comprises at least one genetic variation that inhibits SBEIIa and/or SBEIIb expression and/or activities in the endosperm. The genetic variation may be any genetic variation or combination of genetic variations that leads to a reduction in both SBEIIa and SBEIIb activities and/or proteins in rice endosperm, such as mutations in the SBEIIa and SBEIIb genes, an introduced nucleic acid such as a gene encoding an antisense, enhanced antisense, co-suppression, ribozyme, duplex RNA or similar molecule that inhibits SBEIIa and/or SBEIIb expression or activity, and a combination of the above. The genetic variation is preferably a mill mutation. Plants having reduced SBEIIa and SBEIIb activities may be produced by crossing a plant reduced for SBEIIa with a plant reduced for SBEIIb, or by introducing a transgene encoding a molecule that inhibits expression of both SBEIIa and SBEIIb genes. In a preferred embodiment, the rice plant has null mutations in both SBEIIa and SBEIIb.

The invention also provides rice plants with reduced levels of both SBEIIa and SBEIIb activities in the endosperm during at least some of the development of the grain, the rice plant being capable of bearing grain having starch comprising an increased proportion of amylose compared to starch extracted from equivalent, but unaltered, plant. Preferably, the levels of SBEIIa and SBEIIb are reduced in the endosperm by at least 50%, more preferably by at least 75% and most preferably by at least 90% or 95% compared to the wild-type. The term "wild-type" has its normal meaning in the field of genetics and includes rice cultivars or genotypes which are not modified as taught herein.

The invention also provides progeny plants and grain which have the desired characteristics of the parent rice plants, in genotype and/or phenotype. The invention also extends to any propagating material of the rice plants that can be used to produce the plants with the desired characteristics, such as cultured tissue or cells.

The altered rice plants of the invention may be crossed with plants containing a more desirable genetic background, and therefore the invention includes the genetic variation(s) in other genetic backgrounds. After the initial crossing, a suitable number of backcrosses may be carried out to remove the less desirable background. The desired genetic background may include a suitable combination of genes providing commercial yield and other characteristics such as agronomic performance or abiotic stress resistance. The genetic background might also include other altered starch biosynthesis or modification genes, for example genes from other rice lines that have a shrunken endosperm where the causal gene is not known.

In a preferred embodiment, the rice plant comprises the $Wx^a$ allele of the waxy gene. This allele is found mostly in Indica varieties of rice, while the $Wx^b$ allele 13 found mostly in Japonica varieties. The $Wx^b$ allele carries a substitution mutation (GT to TT) at the 5' splice site of the first intron of the waxy gene, resulting in lower waxy gene expression and therefore lower GBSS activity and lower amylose levels than in corresponding plants containing the $Wx^a$ allele (Isshiki et al., 1998; Hirano et al., 1998; Frances et al., 1998).

The plants or grain therefrom may be transgenic or non-transgenic.

Grain

The invention also provides rice grain comprising an altered starch compared to starch extracted from an equivalent, but unaltered, rice plant. Grain is defined herein as essentially mature grain. This includes grain as harvested in a commercial setting. At harvest, rice gain may be in the form of rough rice, which includes the hull, or "brown rice" where the hull is removed. Only the brown rice fraction is edible. Brown rice consists of the outer layers of pericarp, seed-coat and nucellus, the germ (embryo) and the endosperm. The endosperm as defined herein consists of the aleurone layer and the endosperm proper, consisting of the subaleurone layer and the starchy or inner endosperm. Brown rice may be milled by abrasive or friction milling to remove the pericarp, seed-coat, testa, aleurone layer and embryo to yield milled rice, which essentially comprises the starchy endosperm. Milling results in loss of the constituents of the seed-coat and aleurone including some of the fat, protein, fiber, minerals and vitamins including thiamine, riboflavin, niacin and a-tocopherol. The carbohydrate content, mainly starch, is higher in milled rice than in brown rice. Milled wild-type rice grain contains about 77-89% carbohydrate, 6.3-7.1% protein, 1.5-1.7% lipid including both starch-bound and non-starch forms, 0.3-0.8% minerals, 0.3-0.5% crude fibre, 0.7-2.3% neutral detergent fiber and may contain moisture of about 10-15%. "Rice grain" or simply "rice" as defined herein includes rough rice, brown rice and milled rice, and is preferably milled rice.

The rice grain of the invention comprises at least one genetic variation as defined herein for the rice plant from which the grain is derived. The genetic variation(s) lead to a reduction in SBEIIa and SBEIIb activities and/or proteins during development of the endosperm of the rice grain. The grain comprises an increased proportion of amylose (as a percentage of total starch) and a reduced proportion of amylopectin compared to grain from the equivalent, but weltered, plant Starch is the major constituent of milled rice, comprising about 90% of the dry matter. The amylase content of the endosperm starch of rice which is not modified according to the invention is in the range 0-3776, depending on the genotype. Based on iodometric (calorimetric) assays which measure the "apparent amylose content", milled rice is classified as waxy (1-2% amylose), very low amylose (2-12%), low amylose (12-20%), intermediate amylose (20-25%) and high amylose (25-33%), (Juliano, 1979, 1985). Recent studies using HPLC assays showed that the maximum true amylose content is about 20% and that additional iodine binding is due to the long linear chains in amylopectin (Takeda et al., 1987). The "amylose content" or "apparent amylose content" as defined herein is determined by an iodometric method, as known to those skilled in the art, for example the spectrophotometric method described by Morrison and Laignelet (1983). It will be appreciated that other methods such as the high-performance liquid chromatography (HPLC, for example, Batey and Currin, 1996) methods which assay only the "true amylase" may underestimate the amylose content as defined herein.

The grain of the invention has starch comprising at least 40% (w/w) amylose. The proportion of amylose is preferably at least 45%, 50% or 55% of the total starch, more preferably at least 60% and even more preferably at least 65%, 70%, or 75%. In a preferred embodiment, the grain is non-transgenic and its starch comprises at least 40% amylose. Alternatively, the grain has reduced levels of SBEIIa and SBEIIb proteins and its starch has at least 40% amylose. Increased amylose levels may be evidenced by abnormal starch granule morphology or loss of birefringence of the granules when observed under a light microscope or other methods known in the art.

In a preferred embodiment, the rice is of an Indica variety or comprises the Wx$^a$ allele of the waxy gene.

The grain may comprise starch that has altered physical characteristics, for example increased or decreased gelatinisation temperatures and/or altered swelling characteristics during and following gelatinisation.

The grain may be shrunken or non-shrunken, preferably having a non-shrunken phenotype. "Non-shrunken" as used herein is defined as where the majority of grains, preferably at least 90% of the individual grains, show a plump or fully-filled phenotype. This is usually associated with a normal or near normal level of starch accumulation. In contrast, a "shrunken" phenotype as used herein refers to the majority of grains, particularly at least 90% of the grains, having reduced starch accumulation. Slightly shrunken grain refers to a reduction in average starch content of at least 30%, moderately shrunken grain refers to a reduction in average starch content of at least 50%, and highly shrunken grain refers to a reduction in average starch content of at least 70%. Shrunkenness may also be measured by the relative starch content, as a percentage of mature grain weight. The parameters for wild-type brown rice grain size and shape may be defined as extra long, >7.50 rain; long, 6.61 to 7.50 mm; medium, 5.51 to 6.60 mm; and short, <5.50 mm. Grain shape may be characterized based on length-to-width ratio and is defined as slender, >3.0; medium, 2.1 to 3.0; bold 1.1 to 2.0; and round, <1.0. Each of these characteristics may be altered in the rice grain of the invention.

The invention also provides flour, meal or other products produced from the grain. These may be unprocessed or processed, for example by fractionation or bleaching. The invention further provides rice grain useful for food production obtained from the rice plant of the invention. Additionally the invention encompasses grain that has been processed in other ways, so that the grain may have been milled, ground, rolled, pearled, lobbied or cracked, or boiled.

Starch

In another aspect, the invention provides starch granules or starch obtained from the grain of the rice plant as described above, having an increased proportion of amylose and a reduced proportion of amylopectin. The plant from which the grain was obtained has reduced levels of SEIIa and SBEIIb activities in the endosperm and more preferably the activity of SBEI is also reduced. In another aspect, the invention provides starch granules or starch obtained from the grain of the rice plant, comprising at least 40% amylase, preferably at least 45%, 50%, 55% or 60% amylose, and even more preferably at least 65%, 70%, or 75% amylose. Purified starch may be obtained from grain by a milling process, for example a wet milling process, which involves the separation of the starch from protein, oil and fiber. The initial product of the milling process is a mixture or composition of starch granules, and the invention therefore encompasses such granules.

Starch granules of wild-type rice are polyhedral in shape and mainly 3 to 9 μm in size, averaging about 5 μm with unimodal distribution in size. Protein occurs mainly in the form of spherical protein bodies 0.5 to 4 μm in size throughout the endosperm.

The starch may have an increased or reduced gelatinisation temperature, preferably an increased gelatinisation temperature. The gelatinisation temperature, in particular the temperature of onset of the first peak or the temperature for the apex of the first peak, may be elevated by at least 3° C., preferably at least 5° C. or more preferably at least 7° C. as measured by DSC compared to starch extracted from a similar, but unaltered grain. The starch may comprise an elevated level of resistant starch, with an altered structure indicated by specific physical characteristics including one or more of the group consisting of physical inaccessibility to digestive enzymes which may be by reason of having altered starch granule morphology, the presence of appreciable starch associated lipid, altered crystallinity, and altered amylopectin chain length distribution. The high proportion of amylose also contributes to the level of resistant starch.

The invention also provides starch from grain of the exemplified rice plant comprising increased amounts of dietary fibre, preferably in combination with an elevated level of resistant starch. This increase is also at least in part a result of the high relative level of amylose.

Methods of Reducing Gene Activity: Transgenes

The activity of SBEIIa, SBEIIb or other starch biosynthesis or modification genes are preferably altered by introducing a genetic variation into the rice plant. This may be by means of the introduction of a transgene into the rice plant A "genetic variation" means any alteration in the gannets which, in this context, leads to a reduction in the activities of SBEIIa and SBEIIb and optionally other starch biosynthesis or modification genes, and includes mutations such as point mutations, substitutions, inversions, duplications, translocations and preferably deletions, as well as introduction of transgenes into genes or control elements. In a preferred embodiment, the genetic variation is a null mutation, for example as a consequence of an inversion, duplication, translocation, deletion, frameshift or RNA splicing mutation. A "transgene" as referred to herein has the normal meaning in the art of biotechnology and includes a genetic sequence which has been produced or altered by recombinant DNA or RNA technology and which has been introduced into the organism or cell of interest. The transgene may include genetic sequence derived from the organism or cell, for example an antisense sequence. In a preferred embodiment, the transgene comprises a nucleotide sequence having at least 19 consecutive nucleotides having at least 94% identity with at least 19 consecutive nucleotides of the complement of the rice SBEIIa sequence defined herein or the rice SBEIIb sequence defined herein. The transgene typically includes an exogenous nucleic acid which is not derived from rice. "Transgenic" refers to the rice plant or grain or cell containing a transgene. "Non-transgenic" refers to the absence of any transgene in the genome of the rice plant, grain or cell. A transgene is preferably integrated into the genome of the rice plant, grain or cell, for stable inheritance.

Reference herein to a "gene" including an SBEIIa, SBEIIb or other starch biosynthetic gam or genes encoding antisense, enhanced antisense, co-suppression, ribozyme, duplex RNA molecules or the like is to be taken in its broadest context and includes a genomic gene as well as mRNA or cDNA corresponding to the coding regions (i.e. exons) of the gene, if they are present, transcribed but not translated sequences, and regulatory regions including promoters and transcription terminators/polyadenylation sequences. The term "gene" is also used to describe synthetic or fusion molecules encoding all or part of a functional product. Preferred genes are derived from naturally occurring SBEIIa, SBEIIb or starch biosynthetic genes by standard recombinant techniques. Generally, a gene may be subjected to mutagenesis to produce single or multiple nucleotide substitutions, deletions and/or additions. Nucleotide insertional derivatives of such genes include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid. Typical conservative substitutions are those made in accordance with the following:

Suitable Residues for Amino Acid Substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Those skilled in the art will be aware that expression of a gene, or a complementary sequence thereto, in a cell, requires said gene to be placed in operable connection with a promoter sequence. The choice of promoter for the present purpose may vary depending upon the level of expression required and/or the tissue, organ or cell in which expression is to occur, particularly endosperm specific promoters.

Placing a nucleic acid molecule under the regulatory control of a promoter sequence means positioning said molecule such that expression is controlled by the promoter sequence. A promoter is usually, but not necessarily, positioned upstream, or at the 5'-end, of the nucleic acid molecule it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include promoters derived from the genes of viruses, yeast, moulds, bacteria, insects, birds, mammals and plants, preferably those capable of functioning in plant cells, more preferably those capable of being expressed in the endosperm of rice. The promoter may regulate expression constitutively, or differentially, with respect to the tissue in which expression occurs. Alternatively, expression may be differential with respect to the developmental stage at which expression occurs, or in response to external stimuli such as physiological stresses, or temperature.

The method of reducing SBEIIa or other starch biosynthetic gene activity may comprise the step of introducing a transgene into a regenerable cell of rice and regenerating a transgenic rice plant from the transformed cell. The branching enzymes involved in synthesis of amylopectin include SBEI, SBEIIa and SBEIIb and the transgene(s) may inactivate more than one of these genes. Moreover, the inactivation of SBEIIb and/or SBEI may be direct, in that the transgene (e.g. encoding duplex RNA, antisense, or ribozyme RNA, see below) directly targets the SBEIIb or SBEI gene expression, or it may indirectly result in the reduction in the expression of SBEIIb or SBEI. For example, the transgene RNA may target only the SBEIIa gene/RNA in terms of sequence identity or basepairing but also result in reduction of SBEIIb or SBEI activity by altering protein stability or distribution in the endosperm. Additional forms of the present invention reside in the combination of reduced activity of SBEIIa and SBEIIb and an alteration of one or more other amylopectin synthesis enzymes, which enzymes may include SSI, SSII, SSIII, and debranching enzymes such as isoamylase or pullulanase. Expression of any or all of these may be altered by introduction of a transgene. In a particular embodiment, ADP-glucose pyrophosphorylase (ADGP) is overexpressed in the rice plants, which has been shown to enhance yield and growth (Smidansky et al. 2003).

Several DNA sequences are known for amylopectin synthesis genes in rice, any of which can be the basis for designing transgenes for inactivation of the genes in rice. These include rice cDNAs SBEIIa (GenBank accession number E14723, Japanese patent application No. JP1998004970), SBEIIb (D16201, Mizuno et al., 1993) and SBEI (D11082, Mizuno et al., 1992; D10752, Nakamura and Yamanouchi, 1992). The SBEI gale of rice is described in Rahman et al., (1997) and Rahman et al., (1999), or Accession No. D10838, Kawasaki et al., 1993). Further gene sequences may be obtained from the following websites: ncbi.nlm.nih.gov/; tigr.org; gramene.org/about/index.html.

Homologues of SBEIIa, SBEIIb or other amylopectin synthesising genes from wheat, barley, maize or other closely related species can also be used to modify gene expression levels in rice. Such genes or fragments thereof can be obtained by methods well known in the art, including PCR amplification or hybridization to labeled probes. The region(s) of the homologues used in preparing the trample construct should have at least 85% identity to the corresponding rice gene, preferably at least 90% and even more preferably 95-100% identity in the appropriate region. It is also preferred that the transgene specifically target the amylopectin synthesis genes expressed in the endosperm of rice and have less or minimal effect on amylopectin synthesis elsewhere in the plant. This may be achieved by use of suitable regulatory sequences such as endosperm-specific promoters in the transgene.

"Stringent hybridization conditions" as used herein means that hybridization will generally occur if there is at least 90% and preferably at least 95% sequence identity between the probe and the target sequence. Examples of stringent hybridization conditions are overnight incubation in a solution comprising 50% formamide, 5×SSC (1×SSC 150 mM NaCl, 15 mM trisodium citrate), 50 mM sodium phosphate (pH 7.6), 5×Denhardt's solution, 10% dextran sulfate, and 20 µg/ml denatured sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

Antisense

Known genetic engineering or transgenic approaches to altering, in particular specifically reducing, gene activity in plants are well known in the art. These methods of introducing genetic variation into the rice plant include the expression of a suitable antisense molecule that is complementary to the RNA of the target gene and can hybridize with it. Antisense molecules are thought to interfere with the translation or processing or stability of the mRNA of the target gene, thereby inactivating its expression. Methods of devising antisense sequences are well known in the art and examples of these are can be found in U.S. Pat. No. 5,190,131, European patent specification 0467349-A1, European patent specification 0223399-A1 and European patent specification 0240208, which are incorporated bean by reference. The use of antisense techniques in plants has been reviewed by Bourque (1995) and Senior (1998). Bourque lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior (1998) states that antisense methods are now a very well established technique for manipulating gene expression.

Antisense molecules for rice SBEIIa, SBEIIb, SBEI or other amylopectin biosynthesis genes can be based on the rice mRNA sequences or based on homologies with DNA or mRNA sequences derived from other species, for example barley. These antisense sequences may correspond to the structural genes or for sequences that effect control over the gene expression or splicing event. For example, the antisense sequence may correspond to the targeted coding region of the rice SBEIIa or other gene, or the 5'-untranslated region (UTR) or the 3'-UTR or combination of these. It may be complementary in part to intron sequences, which may be spliced out during or after transcription, preferably only to axon sequences of the target gene. In view of the generally greater divergence of the UTRs, targeting these regions provides greater specificity of gene inhibition. The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of homology of the antisense sequence to the targeted transcript should be at least 85%, preferably at least 90% and more preferably 95-100%. The antiserum RNA molecule may of course comprise unrelated sequences which may function to stabilize the molecule.

Cosuppression

Another molecular biological approach that may be used is co-suppression. The mechanism of co-suppression is not well understood but is thought to involve post-transcriptional gene silencing (PTGS) and in that regard may be vary similar to many examples of antisense suppression. It involves introducing an extra copy of a gene or a fragment thereof into a plant in the sense orientation with respect to a promoter for its expression. The size of the sense fragment, its correspondence to target gene regions, and its degree of homology to the target gene are as for the antisense sequences described above. In some instances the additional copy of the gene sequence interferes with the expression of the target plant gene. Reference is made to patent specification WO 97/20936 and European patent specification 0445572 for methods of implementing co-suppression approaches.

Double Stranded RNA-Mediated Gene Silencing

A further method that might be employed to introduce genetic variation into the rice plant is duplex or double stranded RNA mediated gene silencing. This method also involves PTGS. In this method a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing (Smith et al., 2000). The double-stranded region may comprise one or two RNA molecules, transcribed from either one DNA region or two. The presence of the double stranded molecule triggers a response from an endogenous plant system that destroys both the double stranded RNA and also the homologous RNA transcript from the target plant gene, efficiently reducing or eliminating the activity of the target gene. Reference is made to Australian Patent specification 99/292514-A and patent specification WO 99/53050 for methods of implementing this technique. The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of homology of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

The antisense, cosuppression or double stranded RNA molecules may also comprise a largely double-stranded RNA region, preferably comprising a nuclear Localization signal, as described in PCT/AU03/00292. In a preferred embodiment, the largely double-stranded region is derived from a PSTVd type viroid or comprises at least 35 CUG trinucleotide repeats.

Ribozymes

Ribozymes may be used to introduce the genetic variation responsible for inactivation of the desired gene expression in rice. Ribozymes are RNA molecules with enzymatic or catalytic function that can cleave other RNA molecules at specific sites defined by one or often two hybridizing sequences. The cleavage of the RNA inactivates the expression of the target gene. The ribozymes may also act as an nonsense molecule, which may contribute to the gene inactivation. The ribozymes contain one or more catalytic domains, preferably of the hammerhead or hairpin type, between the hybridizing sequences. Other ribozyme motifs may be used including RNAseP, Group I or II introns, and hepatitis delta virus types. Reference is made to European patent specification 0321201 and U.S. Pat. No. 6,221,661. The use of ribozymes to inactivate gams in transgenic plants has been demonstrated, for example by Wegener et al (1994).

Generic Constructs/Vectors

The invention also provides isolated nucleic acid molecules including RNA and preferably DNA which encode the gene-inhibiting molecule. Preferably, the nucleic acid molecules encode the antisense, sense (co-suppression), double-stranded RNA or ribozyme molecules targeting the rice SBEIIa and/or SBEIIb gene sequences and effective in inactivating their expression in endosperm of rice grain. The invention also provides genetic constructs comprising the isolated nucleic acid molecule, comprising one or more regulatory elements such as promoters, enhancers and transcription termination or polyadenylation sequences. Such elements are well known in the art. The genetic constructs may also comprise intron sequences that aid expression of the transgene in plants, particularly in monocotyledonous plants such as rice. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. In a particular embodiment, introns that direct endosperm-specific expression such as the barley SBEII gene intron (Ahlandsberg et al. 2002) are used.

The invention further provides vectors, for example plasmid vectors, comprising the genetic constructs. The term "vector" includes an expression vector, being capable of in vitro or in vivo expression, and a transformation vector, capable of being transferred from one cell or organism to another. The vectors comprise sequences that provide for replication in cells, for example in prokaryotic cells such as *E. coli* or *Agrobacterium*. Preferably, the vector is a binary vector comprising a T-DNA sequence, defined by at least one T-DNA border sequence, that can be introduced into rice cells. The invention further provides cells comprising the vectors, for example *Agrobacterium* or rice cells which may be regenerable cells such as the cells of the scutellum of immature embryos or embryogenic callus. Alternatively, the cells may be transformed rice cells comprising the transgene.

Promoters/Terminators

The transgene or other genetic construct of the invention may include a transcriptional initiation region (promoter) that may provide for regulated or constitutive expression in the endosperm of rice. The promoter may be tissue specific, conferring expression selectively or exclusively in the endosperm. The promoter may be selected from either endosperm-specific (such as High Molecular Weight Glutenin promoter, the rice SSI promoter, rice SBEII promoter, rice GBSS promoter) or promoters not specific for the endosperm (such as ubiquitin promoter or CaMV35S or enhanced 35S promoters). The promoter may be modulated by factors such as temperature, light or stress. Ordinarily, the promoter would be provided 5' of the genetic sequence to be expressed. The construct may also contain other elements that enhance transcription such as the nos 3' or the ocs 3' polyadenylation regions or transcription terminators. The regions of DNA illustrated will be incorporated into vectors containing suitable selectable marker gene sequences and other elements, or into vectors that are co-transformed with vectors containing these sequences.

Transformation Methods for Rice

Methods for transformation of rice, that is for introducing genetic variation into the plant by introduction of an exogenous nucleic acid, are well known in the art, see for example, Chan et al., 1993; Hiei et al., 1994', Zhang et al., 1997; Buchholz et al., 1998.

Transformation may be mediated by suitable *Agrobacterium* strains, or by biolistic methods, or by polyethylene glycol mediated uptake into rice protoplasts, or the like, as known in the art. Vectors carrying the desired nucleotide sequence or genetic construct and a selectable marker may be introduced into regenerable rice cells of tissue cultured plants or explants, for example protoplasts or immature embryos or callus. The selectable marker gene may provide antibiotic or herbicide resistance to the rice cells, or allow the utilization of substrates, for example mannose, for growth. The selectable marker preferably confers geneticin, hygromycin or phosphinothricin resistance to the rice cells. The regenerable rice cells are preferably from the scutellum of immature embryos, mature embryos, caller derived from these, or the meristematic tissue. Transformed cells are selected and then regenerated by methods well known in the art, such as described in Example 2, to produce transformed rice plants.

The transformed plant may contain a selectable marker gene, or such gene may be removed during or after regeneration, for example by excision of the selectable marker gene out of the gamma or by segregation of the selectable marker gene away from the transgene that leads to inhibition of SBEIIa and/or SBEIIb.

Plants where the transgene or mutation has been integrated into a chromosome can be screened for by, for example, using a suitable nucleic acid probe specific for the transgene or phenotypic observation. Any of several methods may be employed to determine the presence of a transformed plant. For example, polymerase chain reaction (PCR) may be used to amplify sequences that are unique to the transformed plant, with detection of the amplified product by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which am transformed or mutant may also be identified i.e. distinguished from non-transformed or wild-type plants by their phenotype, for example conferred by the presence of a selectable marker gene, or the presence of a particular protein by immunological methods, or by the absence of a protein, for example that absence of the SBEIIa protein in the endosperm as detected by ELISA assay or Western blot analysis. An indication used in screening such plants might also be by observation of the phenotypic trait, of the grain, for example by visual inspection or measurement of shrunken grain, or testing for elevated amylose content, or checking microscopically for the presence of birefringence of starch granules.

Mutation

Introduction of the genetic variation leading to reduced activity of the SBEIIa and SBEIIb enzymes or other starch biosynthetic enzyme in the rice endosperm may also be achieved by the appropriate mutations within the respective gene or regulatory sequences of the gene. The extent to which the gene is inhibited will to some degree determine the characteristics of the starch made. The mutations may be truncation or null mutants and these are known to have a significant impact on the nature of the starch, however an altered starch structure will also result from a leaky mutant that sufficiently reduces amylopectin synthesis enzyme activity to provide the characteristic of interest in the starch or grain of rice. Other chromosomal rearrangements may also be effective and these might includes deletions, inversions, duplication or point mutations.

Mutagenesis can be achieved by chemical or radiation means, for example EMS or sodium azide (Zwar and Chandler, 1995) treatment of seal, or gamma irradiation. For gamma ray induced mutation, seeds may be irradiated at a dose of 20-50 kR from $^{60}$Co source (Zikiryaeva and Kasimov, 1972). EMS mutagenesis may be performed by treating the seeds with EMS (0.03%, v/v) as per Mullins et al., (1999). Isolation of mutants may be achieved by screening mutagenised plants or seed. For example, a mutagenized population of rice may be screened for high amylose content in the grain and/or longer than normal amylopectin chain length distribution, or loss of the SBEIIa and/or SBEIIb proteins by ELISA, or for altered grain morphology (Green et al., 1997). Screening is preferably done in a rice genotype that already lacks one of the SBE activities, for example in a SBEIIa- or SBEIIb-negative background. Such mutations may then be introduced into desirable genetic backgrounds by crossing the mutant with a plant of the desired genetic background and performing a suitable number of backcrosses to cross out the originally undesired parent background. Preferred mutations are those which affect the expression or activity of both SBEIIa and SBEIIb in rice.

The invention thereby provides high amylose, non-transgenic rice grain and products therefrom.

Mutations in the genes encoding the SBEIIa, SBEIIb or other enzymes involved in amylopectin synthesis, for example increased levels of GBSS, provide an increased proportion of amylose in starch of the rice endosperm. The amount of amylose per individual grain may be increased as a consequence of diverted carbon flow from amylopectin to amylose, or it may be decreased if there is a significant decrease in starch production per grain. In either case, the relative level of amylose as a percentage of starch increases.

Seed with starch granules having a distorted shape have been reported in high amylose barley (Morell et al, 2003) and in low amylopectin (LAPS) maize baying about 90% amylose in starch (Sidebottom et al., 1998). This phenotype can be used in screening a mutagenised population of rice. Birefringence can also be used for this. Birefringence is the ability of a substance to refract light in two directions; this produces a dark cross called a "maltose cross" on each starch granule when viewed with a polarizing microscope. Birefringence is an indicator of the degree of ordered structural organization of the polymers within the granules (Thomas and Atwell, 1999). Loss of birefringence in starch granules is generally well correlated with increased amylose content.

Suitable for Food Production

In another aspect, the invention provides rice that is useful for food production, the grain having starch comprising a high relative amylose content and a reduced amylopectin content. Preferably the rice plant from which the grain is obtained has a reduced level of SBEIIa and SBEIIb proteins and/or activities in the endosperm during development. The rice plant of the present invention is useful for food production and in particular for commercial food production.

The desired genetic background of the rice will include considerations of agronomic yield and other characteristics. Such characteristics might include agronomic performance, disease resistance and abiotic stress resistance. In Australia one might want to cross the altered starch trait into rice claims such as Amaroo, Ali Combo, Basmati, Bogan, Bombia, Doongara, Goolarah, Illabong, Jarrah, Koshihikari, Kyeema, Langi, Millin, Namage, Opus, Pelde or other commonly grown varieties. The examples provided are suitable for an Australian production region, and other varieties will be suited for other growing regions. It is preferred that the rice variety of the invention provide a yield not less than 80% of the corresponding wild-type variety in at least some growing regions, more preferably not less than 90% and even more preferably not less than 95%. The yield can readily be measured in controlled field trials.

The starch content of the grain should be at least about 25%, preferably at least 35% or 45% and more preferably near to the wild-type levels of 55 to 65% (w/w). Most preferably, the grain has a starch content of at least 90% that of grain from an equivalent, but unaltered, rice. Lower starch contents than wild-type are likely a consequence of reduced amylopectin levels. Even with lower starch contents, the grain may still be undid for commercial food production because of the relatively high value of the high amylose products. Other desirable characteristics include the capacity to mill the grain, in particular the grain hardness. Another aspect that might make a rice plant of higher value is the degree of starch extraction from the grain, the higher extraction rates being more useful. Grain shape is also another feature that can impact on the commercial usefulness of a plant, thus grain shape can have an impact on the ease or otherwise with which the grain can be milled. For example, an elongated grain morphology may make it difficult to mill and process.

Starch may be readily isolated from rice grain using standard methods, for example by wet milling of brokers with alkali solution (sodium hydroxide) to remove protein. Brokens are steeped in alkali solution for 24 hours and are then wet milled in pin mills, hammermills or stone-mill disintegrators with the alkali solution. After the batter is stored for 10 to 24 hours, fiber is removed by passing it through screens, the starch collected by centrifugation, washed thoroughly with water and dried.

Physical Characteristics of the Altered Starch

In another aspect of the invention, the rice starch may have an altered gelatinisation temperature, which may be readily measured by differential scanning calorimetry (DSC). Gelatinisation is the heat-driven collapse (disruption) of molecular order within the starch granule in excess water, with concomitant and irreversible changes in properties such as granular swelling, crystallite melting, loss of birefringence, viscosity development and starch solubilisation. The gelatinisation temperature may be either increased or decreased compared to starch from wild-type plants, depending on the chain length of the remaining amylopectin. High amylose starch from ae (amylose extender) mutants of maize showed a higher gelatinisation temperature than normal maize (Fuwa et al, 1999, Krueger at al., 1987). On the other hand, starch from barley serif mutants that lack starch synthase IIa activity had lower gelatinisation temperatures and the enthalpy for the gelatinisation peak was reduced when compared to that from control plane (Morell et al., 2003).

The altered gelatinisation temperature may be in addition to the relatively high amylose content. The gelatinisation temperature of wild-type rice starch is typically about 61-67° C. (Rahman et al, 2000) for the temperature of the first peak, defined as the onset temperature, as measured by differential scanning calorimetry.

The starch may also be characterized by its swelling rate in heated excess water compared to wild-type starch. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. A low swelling characteristic is useful where it is desired to increase the starch content of a food preparation, in particular a hydrated food preparation.

The starch structure of the rice of selected forms of the present invention may also differ in that the degree of crystallinity is reduced compared to normal starch isolated from rice. The reduced crystallinity of a starch is also thought to be associated with enhance organoleptic properties and contributes to a smoother mouth feel. Thus the starch may additionally exhibit reduced crystallinity resulting from reduced levels of activity of one or more amylopectin synthesis enzymes. Crystallinity is typically investigated by X-ray crystallography.

One measure of an altered amylopectin structure is the distribution of chain lengths, or the degree of polymerization, of the starch. The chain length distribution may be determined by using fluorophore-assisted carbohydrate electrophoresis (FACE) following isoamylase de-branching. The amylopectin of the starch of the invention may have a distribution of chain length in the range from 5 to 60 that is greater than the distribution of starch from wild-type plants upon debranching. Starch with longer chain lengths will also have a commensurate decrease in frequency of branching. Thus the starch may also have a distribution of longer amylopectin chain lengths in the amylopectin still present.

Food Characteristics

Rice starch is a major source of carbohydrate in the human diet, particularly in Asia, and the grain of the invention and products derived from it can be used to prepare food. The food may be consumed by man or animals, for example in livestock production or in pet-food. The grain derived from the altered rice plant can readily be used in food processing procedures, and therefore the invention includes milled, ground, kibbled, cracked, rolled, boiled or parboiled grain, or products obtained from the processed or whole grain of the rice plant, including flour, brokers, rice bran and oil. The products may be precooked or quick-cooking rice, instant rice, granulated rice, gelatinized rice, canned rice or rice pudding. The grain or starch may be used in the production of processed rice products including noodles, rice cakes, rice paper or egg roll wrapper, or in fermented products such as fermented noodle or beverages such as sake. The grain or starch derived therefrom may also be used in, for example, breads, cakes, crackers, biscuits and the hire, including where the rice flour is mixed with wheat or other flours, or food additives such as thickeners or binding agents, or to make drinks, noodles, pasta or quick soups. The rice products are suitable for use in wheatfree diets. The grain or products derived from the grain of the invention are particularly desired in breakfast cereals such as puffed rice, rice flakes or as extruded products. The high amylose starches of the invention can also be used to form high strength gels that are useful in the confectionery industry, or allow lower molding and curing times. They may also be used as a coating, for example to reduce oil absorption in deep-fried potato or other foods.

Dietary Fiber

Dietary fibre, in this specification, is the carbohydrate and carbohydrate digestion products that are not absorbed in the small intestine of healthy humans but enter the large bowel. This includes resistant starch and other soluble and insoluble carbohydrate polymers. It is intended to comprise that portion of carbohydrates that are fermentable, at least partially, in the large bowel by the resident microflora.

The starch of the invention preferably contains relatively high levels of dietary fiber, more particularly amylose. The dietary fiber content of the grain of the present invention may or may not result solely from the increased relative endospermal amylose content.

Aspects of this invention might also arise from the combination of aleurone layer and germ in combination with high levels of dietary fiber. Specifically, this may arise where higher relative levels of aleurone or germ are present in the grain. Where the rice grain is slightly shrunken the endosperm is present in reduced amounts and the aleurone layer and the gam are present in relatively elevated amounts. Thus the rice has a relatively high level of certain beneficial elements or vitamins in combination with elevated resistant starch, such elements include divalent cations, bioavailable $Ca^{++}$ and vitamins such as folate or antioxidants such as tocopherols or tocotrienols. One specific form of milled product might be one where the aleurone layer is included in the milled product. Particular milling process might be undertaken to enhance the amount of aleurone layer in the milled product. Thus any product derived from grain milled or otherwise processed to include aleurone layer and germ will have the additional nutritional benefits, without the requirement of adding these elements from separate sources.

Resistant Starch

Resistant starch is defined as the sum of starch and products of starch digestion not absorbed in the small intestine of healthy humans but entering into the large bowel. Thus, resistant starch excludes products digested and absorbed in the small intestine. Resistant starches include physically inaccessible starch (RS1 form), resistant native starch granules (RS2), retrograded starches (RS3), and chemically modified starches (RS4). The altered starch structure and in particular the high amylose levels of the starch of the invention give rise to an increase in resistant starch when consumed in food. The starch may be in an RS1 form, being somewhat inaccessible to digestion. Starch-lipid association as measured by V-complex crystallinity is also likely to contribute to the level of resistant starch.

It will be understood that one benefit of the present invention is that it provides for products that are of particular nutritional benefit, and moreover it does so without the need to post-harvest modify the starch or other constituents of the rice grain. However it may be desired to make modifications to the starch or other constituent of the grain, and the invention encompasses such a modified constituent. Methods of modification are well known and include the extraction of the starch or other constituent by conventional methods and modification of the starches to increase the resistant form. The starch may be modified by treatment with heat and/or moisture, physically (for example ball milling), enzymatically (using for example α- or β-amylase, pullulanase or the hire), chemical hydrolysis (wet or day using liquid or gaseous reagents), oxidation, cross bonding with difunctional reagents (for example sodium trimetaphosphate, phosphorous oxychloride), or carboxymethylation.

Glycemic Index

Glycaemic Index (GI) relates to the rate of digestion of foods comprising the starch, and is a comparison of the effect of a test food with the effect of white bread or glucose on excursions in blood glucose concentration. The Glycaemic Index is a measure of the likely effect of the food concerned on post prandial serum glucose concentration and demand for insulin for blood glucose homeostasis. One important characteristic provided by foods of the invention is a reduced glycaemic index. Serum glucose levels were lower 30 min after ingestion of high amylose rice products by human volunteers compared to low amylose rice (Goddard et al., 1984). Furthermore, the foods may have a low level of final digestion and consequently be relatively low-calorie. A low calorific product might be based on inclusion of flour produced from milled rice grain. Such foods may have the effect of being filling, enhancing bowel health, reducing the post-prandial serum glucose and lipid concentration as well as providing for a low calorific food product.

Non-Food Applications

The present invention provides modified or improved starches having elevated levels of amylose or reduced levels of amylopectin whose properties satisfy any of various industrial requirements. Starch is widely used in non-food industries, including the film, paper, textile, corrugating and adhesive industries (Young, 1984), for example as a sizing agent. Rice starch may be used as a substrate for the production of glucose syrups or for ethanol production. The physical properties of unmodified starch limits its usefulness in some applications and often imposes a requirement for chemical modification that can be expensive or have other disadvantages. The invention provides starch for which less post-harvest modification may be required, in particular due to the reduced amylopectin content in combination with other physical properties. For example, the pasting temperature, resistance to shearing stresses, film strength and/or water resistance of starches and product made from the grain of this invention may be altered. The starch may also be used to prepare a biodegradable loose-fill packing material that can be used as a replacement for polystyrene or other packing material.

It will be understood that whilst various indications have been given as to aspects of the present invention, the invention may reside in combinations of two or more aspects of the present invention.

EXAMPLES

Example 1

Materials and Methods

Materials and Media

N6 Macro-Elements (20× Stock Solution)

|  | g/l |
| --- | --- |
| $(NH_4)_2SO_4$ | 9.3 |
| $KNO_3$ | 56.6 |
| $KH_2PO_4$ | 8 |
| $MgSO_4 \cdot 7H_2O$ | 3.7 |
| $CaCl_2 \cdot 2H_2O$ | 3.3 |

MS Macro-Elements (20× Stock Solution)

|  | g/l |
| --- | --- |
| $NH_4NO_3$ | 33.0 |
| $KNO_3$ | 38.0 |
| $KH_2PO_4$ | 3.4 |
| $MgSO_4 \cdot 7H_2O$ | 7.4 |
| $CaCl_2 \cdot 2H_2O$ | 8.8 |

N6 Micro-Elements (100× Stock Solution)

|  | mg/100 ml |
| --- | --- |
| $MnSO_4 \cdot 4H_2O$ | 440 |
| $ZnSO_4 \cdot 7H_2O$ | 150 |
| $H_3BO_3$ | 160 |
| KI | 80 |

MS Micro-Elements (1000× Stock Solution)

|  | mg/l |
| --- | --- |
| $MnSO_4 \cdot 4H_2O$ | 22300 |
| $Na_2MoO_4 \cdot 2H_2O$ | 250 |
| $H_3BO_3$ | 6220 |
| $ZnSO_4 \cdot 7H_2O$ | 8600 |
| $CuSO_4 \cdot 5H_2O$ | 25 |
| $CoCl_2 \cdot 6H_2O$ | 25 |
| KI | 830 |

B5 Micro-Elements (100× Stock Solution)

|  | mg/l |
| --- | --- |
| $MnSO_4 \cdot 4H_2O$ | 1000 |
| $Na_2MoO_4 \cdot 2H_2O$ | 25 |
| $H_3BO_3$ | 300 |
| $ZnSO_4 \cdot 7H_2O$ | 200 |
| $CuSO_4 \cdot 5H_2O$ | 3.87 |
| $CoCl_2 \cdot 6H_2O$ | 2.5 |
| KI | 75 |

N6 Vitamins (100× Stock Solution)

|  | mg/100 ml |
| --- | --- |
| Glycin | 20 |
| Thiamine-HCl | 10 |
| Pyridoxine-HCl | 5 |
| Nicotinic acid | 5 |

MS Vitamins (100× Stock Solution)

|  | mg/100 ml |
| --- | --- |
| myo-Inositol | 1000 |
| Thiamine-HCl | 1 |
| Pyridoxine-HCl | 5 |
| Nicotinic acid | 5 |

B5 Vitamins (100× Stock Solution)

|  | mg/100 ml |
| --- | --- |
| Glycine | 1000 |
| Thiamine-HCl | 100 |
| Pyridoxine-HCl | 10 |
| Nicotinic acid | 10 |

MS iron (200× stock solution)

|  | ml/500 ml |
| --- | --- |
| FeCl, (60% w/v) | 2.7 |

MS Na$_2$.EDTA (200× Stock Solution)

|  | g/500 ml |
| --- | --- |
| Na$_2$•EDTA | 3.7 |

A 2,4-dichloro-phenoxyacetic acid (2,4-D) (1 mg/ml, Sigma No. D-6679) stock solution was prepared by dissolving 100 mg of 2,4-D in 1 ml absolute ethanol, adding 3 ml of 1N KOH, and adjusting the pH to 6 with 1N HCl.

Solutions of 6-benzyl amino mine (1 mg/ml BAP, Sigma No. B-3408) and naphthalene acetic acid (1 mg/ml NAA, Sigma No. N-0640) were prepared.

Abscisic acid (ABA, 2.5 mg/ml, Sigma No. A-1049) was prepared by dissolving 250 mg ABA in 2 ml of 1M NaOH, making up to 100 ml with sterile water.

Timentin (150 mg/ml, Smith-Kline Beecham 6571-30) was prepared by dissolving 3.1 g in 20.66 ml of sterile water.

Hygromycin (50 mg/ml) was obtained from Roche (No. 843 555) and other reagents from Sigma.

N6D Media for Callus Induction

|  | amount/litre |
| --- | --- |
| N6 macro (20X) | 50 ml |
| N6 micro (1000X) | 1 ml |
| N6 vitamins (100X) | 10 ml |
| MS iron (200X) | 5 ml |
| MS Na$_2$ EDTA (200X) | 5 ml |
| Myoinositol | 100 mg |
| Casamino acid | 300 mg |
| Proline | 2.9 g |
| 2,4-D (1 mg/ml) | 2 ml |
| Sucrose | 30 g |

The pH was adjusted to 5.8 with 1M KOH, 3 g phytogel added per liter and the mixture autoclaved.

NB Media for Subculturing

|  | amount/liter |
| --- | --- |
| N6 macro-elements (20X) | 50 ml |
| B5 micro-elements (100X) | 10 ml |
| B5 vitamins (100X) | 10 ml |
| MS iron (200X) | 5 ml |
| MS Na$_2$ EDTA (200X) | 5 ml |
| 2,4-D (1 mg/ml) | 2 ml |
| Sucrose | 30 g |
| Proline | 500 mg |
| Glutamine | 500 mg |
| Casein enzymatic hydrolysate (CEH) | 300 mg |

The pH was adjusted to 5.8-5.85 with 1M KOH, 3 g phytogel added per liter, and the mixture autoclaved.

MS Media for Subculturing

|  | amount/liter |
| --- | --- |
| MS macro-elements (20X) | 25 ml |
| MS micro-elements (1000X) | 1 ml |
| MS vitamins (100X) | 10 ml |
| MS iron (200X) | 5 ml |
| MS Na$_2$ EDTA (200X) | 5 ml |
| Sucrose | 10 g |

The pH was adjusted to 5.8-5.85 with 1M KOH, 2.5 g phytogel added per liter, and the mixture autoclaved.

NBO: NB media, plus 30 g/ml mannitol and 30 g/ml sorbitol, added before pH adjustment.

NBHT30: NB media plus 30 mg/l hygromycin and 150 mg/l Timentin added after autoclaving and just before pouring.

NBHT50: NB media plus 50 mg/l hygromycin and 150 mg/l Timentin added after autoclaving and just before pouring.

PRHT50: NB media (with no 2,4-D), plus following added after autoclaving, to a final concentration of BAP (2 mg/l), NAA (1 mg/l), ABA (5 mg/l), Hygromycin (50 mg/l) and Timentin (150 mg/l).

RHT50: NB media (with no 2,4-D), plus following added after autoclaving, to a final concentration of: BAP (3 mg/l), NAA (0.5 mg/l), Hygromycin (50 mg/l), Timentin (150 mg/l).

MST medium: MS medium, with 0.05 mg/l NAA and 150 mg/l Timentin added after autoclaving.

Rice Transformation

Mature grains were dehusked, soaked in 70% ethanol for 1 minute and washed with sterile water 3 times before being soaked in 50% bleach for 30 min. The sterilized grain were washed thoroughly with sterile water under aseptic conditions and then plated onto N6D medium. Plates were sealed with Micropore-tape and incubated under light for 6-8 weeks at 26-28° C. for callus production. Callus was produced, presumably from the scutellum of the embryos, without any dissection of the embryos from the grains. If subculture was required, calli were transferred on to NB medium and the plates sealed with parafilm. The plates were left in the dark at 28° C. in a box covered with aluminum foil. Subcultures were carried out every 4 weeks. Calli were subcultured not more than 5 times before use for transformation.

For *Agrobacterium* mediated transformation, *Agrobacterium* strains containing the gene constructs to be transferred were grown at 28° C. on plates with appropriate antibiotics, and after 2 days growth, the cells scraped off the plates and resuspended in liquid NB medium containing 100 μM acetosyringone. Healthy looking calli were immersed in the bacterial suspension for 10 min, the calli then drained briefly and placed on NBO plates containing 100 μM acetosyringone in the dark at 25° C. for 2 days. This period is referred to as "co-cultivation" in the presence of *Agrobacterium* containing the gene construct. After co-cultivation, the calli were washed in sterile water containing 150 mg/l Timentin, blotted dry briefly, and plated onto NBHT30 (which includes the selective agent hygromycin) plates containing 150 mg/l Timentin. After 3-4 weeks at 26-28° C., any calli showing zones of growth were subcultured onto the same medium for a further 10-24 days. Sustained growth indicated calli resistant to hygromycin, i.e. transformed calli. These calli were transferred onto NBHT50 plates containing timentin and incubated at 26-28° C. in the dark for a further 14-21 days. Healthy looking calli were transferred to PRHT50 plates for a further 8-12 days in the dark. Finally, shoots were regenerated on RHT50 medium in the light at 28° C. for 30 days, or more. Shoots that showed root formation were transferred to ½MST medium and when large enough transferred to soil in the greenhouse. This method has proven successful with a variety of rice cultivars including both japonica and indica types.

Example 2

Construct Preparation for Gene Down-Regulation

Figure 5:
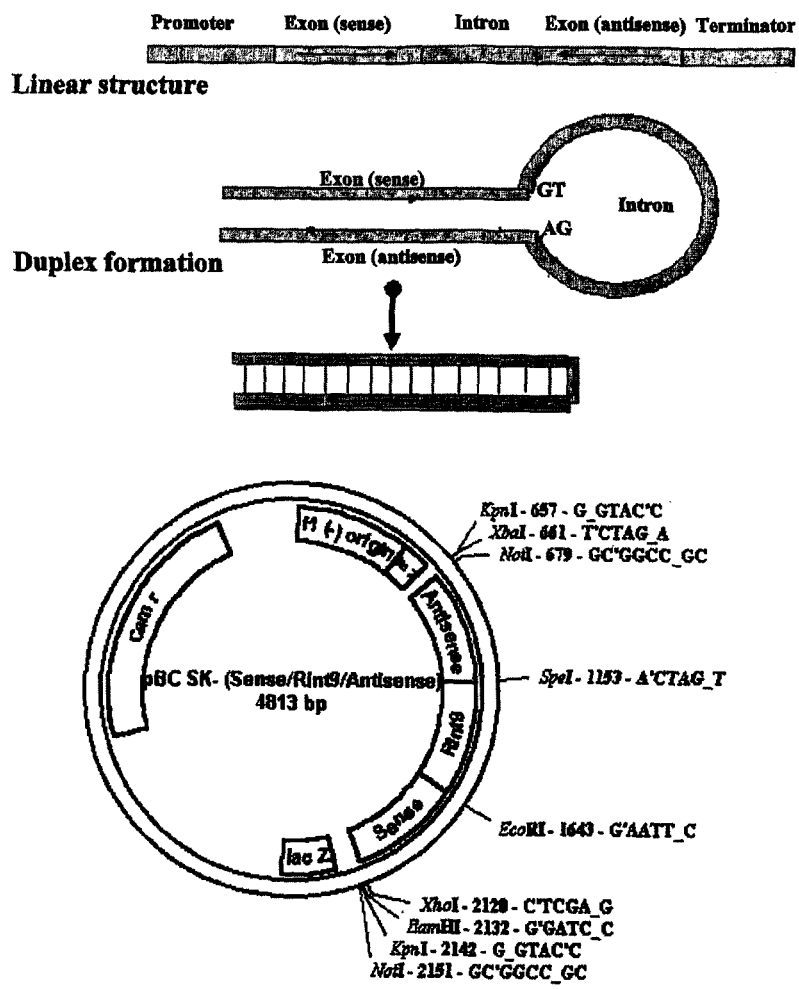
FIG. 5. Schematic of duplex-RNA constructs. A. The order of the gene elements used were promoter, SBEIIa or SBEIIb cDNA sequence in sense orientation, intron (Rint9), SBEIIa or SBEIIb cDNA sequence in antisense orientation, and transcription terminator/polyadenylation sequence. The transcript of the ds-SBEIIa and ds-SBEIIb genes forms a "hairpin" RNA structure with a double-stranded region formed by hybridization between the sense and antisense sequences. The intron sequence bordered by the GT and AG nucleotides is spliced out. A schematic of pRBEI.IR (pBC SK-(sense/Rint9/antisense)) is also shown. Corresponding constructs pRBEIIa.IR and pRBEIIb.IR were also made.
Figure 6:
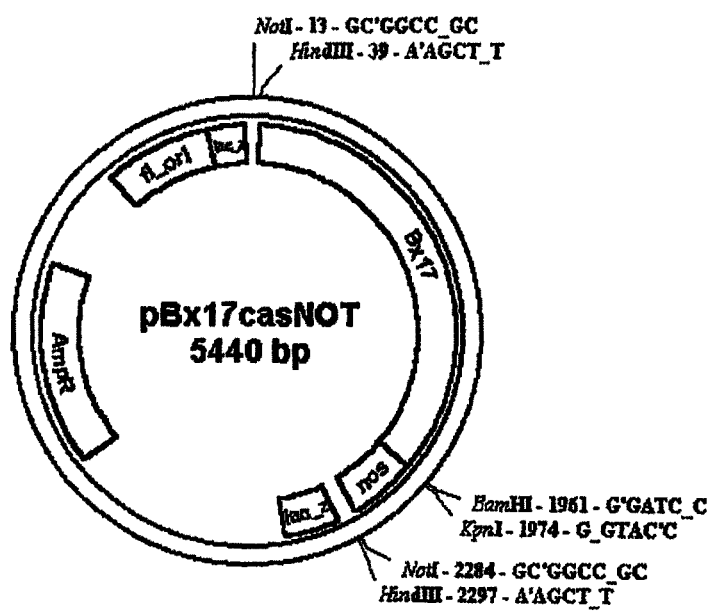
FIG. 6. Schematic of plasmid vector pBx17casNOT is shown.

Segments of the rice SBEI, SBEIIa and SBEIIb genes were amplified by PCR for use in preparation of gene constructs for the down-regulation of gene expression in rice. The segments chosen were from exon regions near the 3' ends of the genes as these regions of the genes are more divergent and this was thought to reduce the likelihood of cross-silencing of the gates by the constructs in transformed rice. The segments amplified were: SBEI-nucleotides 1982-2527 of GenBank accession No. D11082; SBEIIa-nucleotides 2458-2997 of Accession No. AB023498; SBEIIb-nucleotides 2414 to 2912 of Accession No. D16201 (Sequences shown in FIGS. 1-3). The amplified fragments, which contained additional sequences comprising restriction endonuclease sites at the ends for convenience in subsequent cloning steps, were cloned into the plasmid vector pGEM®-T. An intron sequence was also obtained by amplifying the SBEI intron 9 sequence from rice. The fragment included the sequence from nucleotides 9112-9606 of the genomic sequence Genbank Accession No. D10838 and flanking SpeI and EcoRI restriction sites, and was inserted into pBCSK⁻ (Stratagem) to form pRint9_BC (FIG. 4). The exon fragments from the SBEI, SBEIIa and SBEIIb genes were then cloned in the antisense and sense orientations in pRint9_BC using the SpeI/XbaI and XhoI/EcoRI sites, respectively. This served to form an inverted repeat for each of these sequences, each separated by the intron sequence. The resultant plastids were designated pRBEI.IR, pRBEIIa.IR and pRBEIIb.IR (FIG. 5). The chimeric fragments were excised with BamHI and KpnI and inserted into the same sites of pBx17casNOT (FIG. 6). This joined the antisense/intron/sense chimeric fragments to the Bx17 promoter region and the nos3' termination region in the correct orientation for expression. Each expression cassette was then excised by digestion with HindIII and NotI and inserted into the binary vector pWBvec8 (Wang et al. Acta Hort 461:401-407, 1998) which contains a plant expressible hygromycin gene for selection in plant cells as well as a spectinomycin resistance gene for selection in bacteria. The constructs were designated dsSBEI, dsSBEIIa, and dsSBEIIb. These constructs were then transferred to the *Agrobacterium tumefaciens* strain (AGL1) cells (Lazo et al. (1991)) by electroporation.

A further duplex-RNA (dsRNA) construct was made to reduce the expression of the SBEIIa and possibly the SBEIIb genes of rice, using sequences from the corresponding SBEIIa gene wheat. As for the other constructs, above, the desired nucleic acid sequence corresponding to part of the SBEIIa gene occurred in both the sense and antisense orientations relative to the promoter so that the expressed RNA comprised complementary regions that were able to basepair and form a duplex or double-stranded RNA. A spacer region between the sense and antisense sequences comprised an intron sequence which, when transcribed as part of the RNA in the transformed plant, would be spliced out to form a tight "hairpin" duplex structure. The inclusion of an intron has been found to increase the efficiency of gene silencing conferred by duplex-RNA constructs (Smith et al, 2000). The desired nucleic acid was linked to a high molecular weight glutenin (HMWG) promoter sequence from wheat and terminator sequence from the nopaline synthase gene from *Agrobacterium* (nos3'). This provided endosperm specific expression of the dsRNA sequence.

The SBEIIa duplex-RNA construct contained 1536 bp of nucleotide sequence amplified by PCR from the wheat SBEIIa gene (GenBank Accession number AF338431). This included: a 468 bp sequence that comprised the whole of axons 1 and 2 and part of exon 3, with EcoRI and KpnI restriction sites on either side (fragment 1), a 512 bp sequence consisting of part of aeons 3 and 4 and the whole of intron 3 of SBEIIa with KpnI and SacI sites on either side (fragment 2) and a 528 bp fragment consisting of the complete exons 1, 2 and 3 of SBEIIa with BamHI and SacI sites on either side (fragment 3). The sequences used have 80% identity over 217 nucleotides with the rice SBEIIa gene (SBE4), including greater homology over shorter regions (87% over 50 nucleotides and 92% over 27 nucleotides), and it was therefore expected that expression of this sequence in rice endosperm would lead to significant decrease in the expression of rice SBEIIa. The wheat sequence was also 76% identical over 113 nucleotides to rice-branching enzyme-3, the equivalent of SBEIIb, and this was expected to affect the level of this transcript as well.

Fragments 1, 2 and 3 were then ligated so that the sequence of fragment 3 was ligated to fragment 2 in the antisense orientation relative to fragment 1. The duplex-RNA constructs were initially generated in the vector pBx17casNOT (FIG. 6) which contained the HMWG promoter sequence and nos3' terminator. The gene construct in this vector was designated pBx17ds-wSBEIIa and the duplex-RNA gene designated da-wSBEIIa. The cassette including the ds-wSBEIIa gene was inserted into pWBvec8, introduced into *Agrobacterium* strain AGL1 and used to transform rice as described in Example 1.

Example 3

Production of Rice with Reduced SBE Activity

The constructs dsSBEI, dsSBEIIa, is SBEIIb and ds-wSBEIIa in AGL1 cells were used to produce transformed rice plants (cv. Nipponbare) according to the methods described in Example 1. Five hundred rice calli were used for each construct, transformed calli selected and rice plants regenerated. After the plants were transferred to soil, transformation of the plants was demonstrated by PCR or Southern blot hybridization analysis using primers or probes specific for the SBEI, SBEIIa or SBEIIb gene segments used. Of 24 regenerated plants from the transformation with ds-wSBEIIa, 21 were shown to be positive for the introduced SBEIIa sequences.

Grain from the transformed plants (T1 seed) is assayed for SBE proteins by Western blot analysis using specific antibodies to the respective proteins, after gel electrophoresis of endosperm proteins on acrylamide gels. SBE activity is reduced in the majority of transformed lines. The proportion of amylose in starch of the grain is determined. Some of the SBEIIa transformed lines show relative amylase levels of at least 40%, and some of these more than 50%. The proportion of amylose is raised even further when both SBEIIa and SBEIIb activities are reduced.

Example 4

Starch and Protein Analysis

Carbohydrate Determination and Analysis

Starch is isolated from developing endosperm or from mature grain using the methods of Takeda et al., (1986); Lumdubwong et al., (2000); Chien et al (2002) or Schulman et al., (1991). Starch content is determined using the total starch analysis kit supplied by Megazyme (Bray, Co Wicklow, Republic of Ireland). The starch content is then compared to control plants. Subtraction of the starch weight from the total grain weight to give a total non-starch content of the grain determines whether the reduction in total weight is due to a reduction in starch content.

The amylose content of starch samples is determined by the colorimetric (iodometric) method of Morrison and Laignelet (1983) with slight modifications as follows. Approximately 2 mg of starch is weighed accurately (accurate to 0.1 mg) into a 2 ml screw-capped tube fitted with a rubber washer in the lid. To remove lipid, 1 ml of 85% (v/v) methanol is mixed with the starch and the tube heated in a 65° C. water bath for 1 hour with occasional vortexing. After centrifugation at 13,000 g for 5 min, the supernatant is carefully removed and the extraction steps repeated. The starch is then dried at 65° C. for 1 hour and dissolved in urea-dimethyl sulphoxide solution (UDMSO; 9 volumes of dimethyl sulphoxide to 1 volume of 6 M urea), using 1 ml of UDMSO per 2 mg of starch (weighed as above). The mixture is immediately vortexed vigorously and incubated in a 95° C. water bath for 1 hour with intermittent vortexing for complete dissolution of the starch. An aliquot of the starch-UDMSO solution (50 µl) is treated with 20 µl of $I_2$—KI reagent that contains 2 mg iodine and 20 mg potassium iodide per ml of water. The mixture is made up to 1 ml with water. The absorbance of the mixture at 650 nm is measured by transferring 200 µl to a microplate and reading the absorbance using an Emax Precision Microplate Reader (Molecular Devices, USA). Standard samples containing from 0 to 100% amylase and 100% to 0% amylopectin am made from potato amylase and corn (or potato) amylopectin (Sigma) and treated as for the test samples. The Amylase content (percentage amylose) is determined from the absorbance values using a regression equation derived from the absorbances for the standard samples. Analysis of the amylose/amylopectin ratio of non-debranched starches may also be carried out according to Case et al., (1998) or by an HPLC method for separating debranched starches as described by Batey and Curtin (1996).

The distribution of chain lengths in the starch may be analysed by fluorophore assisted carbohydrate electrophoresis (FACE) using a capillary electrophoresis unit according to Morell et al (1998), after debranching of the starch samples. The gelatinisation temperature profiles of starch samples may be measured in a Pyris 1 differential scanning calorimeter (Perkin Elmer, Norwalk Conn., USA). The viscosity of starch solutions may be measured on a Rapid-Visco-Analyaer (RVA, Newport Scientific Pty Ltd, Warriewood, Sydney), for example using conditions as reported by Batey et al., 1997. The parameters that may be measured include peek viscosity (the maximum hot paste viscosity), holding strength, final viscosity and pasting temperature. The swelling volume of flour or starch may be determined according to the method of Konik-Rose et al (2001). The uptake of water is measured by weighing the sample prior to and after mixing the flour or starch sample in water at defined temperatures and following collection of the gelatinized material.

β-Glucan levels may be determined using the kit supplied by Megazyme (Bray, Co Wicklow, Republic of Ireland).
Analysis of Protein Expression in Endosperm.

Specific protein expression in endosperm is analyzed by Western blot procedures. Endosperm is dissected away from all maternal tissues and samples of approximately 0.2 mg are homogenized in 600 µl of 50 mM KPi buffer (42 mM $K_2HPO_4$ and 8 mM $KH_2PO_4$), pH 7.5, containing 5 mM EDTA, 20% glycerol, 5 mM DTT and 1 mM Pefabloc. The ground samples are centrifuged for 10 min at 13,000 g and the supernatant aliquoted and frozen at −80° C. until use. For total protein estimation, a BSA standard curve is set up using 0, 20, 40, 60, 80 and 100 µl aliquots of 0.25 mg/ml BSA standard. The samples (3 µl) are made up to 10014 with distilled water and 1 ml of Coomassie Plus Protein reagent is added to each. The absorbance is read after 5 min at 595 nm, using the zero BSA sample from the standard curve as the blank, and the protein levels in the samples determined. Samples containing 20 µg total protein from each endosperm are run on an 8% non denaturing polyacrylamide gel containing 0.34 M Tris-HCl (pH 8.8), acrylamide (8.0%), ammonium persulphate (0.06%) and TEMED (0.1%). Following electrophoresis, the proteins are transferred to a nitrocellulose membrane according to Morell et al., (1997) and immunoreacted with SBEIIa or SBEIIb specific antibodies.

Example 5

Optimised Gene Silencing of Target Genes by Identification of Unique Sequences in the Rice Genome Genetic sequences used to reduce target gene expression (gene silencing) by methods such as, for example, using duplex RNA, antisense or co-suppression constructs, are preferably highly specific for the target gene. That is, the silencing molecule comprises a nucleotide sequence of at least 19 consecutive nucleotides that is at least about 95% identical to a sequence of at least 19 consecutive nucleotides of the target gene or its complement. Ideally, for maximum specificity, the targeted sequence is unique to the target gene and is not present elsewhere as an expressed gene in the plant genome. This would minimize "off-gene effects". We have used knowledge of the near complete rice genome sequence to compare the SBE target gene sequences with the remainder of the rice genome to identify optimized target sequences within these genes.

A rice genomic DNA sequence database (OSA1.seq) was downloaded from the TIGR website (tigr.org/tdb/e2k1/osa1/) in PASTA format. The database was formatted and made available for BLAST using "formatdb" and for EMBOSS function regret using "dbifasta". Query sequences were created in a FATSA format and used to watch for homologous sequences in the rice genome by running a BLAST based Gene Silencing program (P. Waterhouse et al, CSIRO Plant Industry, personal communication) with a set of preset parameters (Options for compare: word 19 and stringency 18).

The SBEIIa, SBEIIb and SBEI sequences used to prepare gene silencing constructs as described in Example 2 were used as query sequences against the rice gamma. The output is shown in FIG. 8. Multiple "NNNN . . . " in the output sequences indicated that the query sequences in those regions had homology in a region of at least 19 consecutive nucleotides with a sequence elsewhere in the rice genome. It can be seen that the SBEIIa sequence used is unique, the SBEIIb sequence used contains some non-unique sequence, while the SBEI sequence used appears to be duplicated elsewhere in the rice genome except for the terminal 57 nucleotides which appears to be clear (FIG. 8). Examination of the current rice genome sequence revealed that there appears to be an overlapping genomic DNA sequence between two overlapping BAC clones which may include the SBEI gene region. The apparent duplication may be real or may represent an error in the assembly of the rice genome in that region.

REFERENCES

Abel et al., (1996). *The Plant Journal* 10, 981-991.
Ahlandsberg et al, (2002). *Plant Cell Rep* 20, 864468.
Anderson et al., (1989). *Nucl Acids Res* 17, 461-462.
Baba et al., (1991). *Biochem Biophys Res Commun* 181: 87-94.
Baga et al., (2000). *Plant Physiol.* 124, 253-263.
Batey and Curtin. (1996). *Starch* 48, 338-344.
Batey et al., (1997). *Cereal Chemistry* 74, 497-501.
Blauth et al., (2001). *Plant Physiology* 125, 1396-1405.
Bourque. (1995). *Plant Science* 105, 125-149.

Boyer and Preiss, (1978). *Carbohydrate Research* 61, 321-334.
Boyer and Preiss, (1981). *Plant Physiology* 67, 1141-1145.
Boyer et al., (1980). *Starch* 32, 217-222.
Buchholz et al, (1998). *Methods Mol Biol* 81, 383-396.
Buleon et al., (1998). *International Journal of Biological Macromolecules* 23, 85-112.
Cao et al., (2000). *Archives. of Biochemistry and Biophysics.* 373, 135-146.
Case et al., (1998). *Journal of Cereal Science* 27, 301-314.
Chan et al., (1993). *Plant Mal Biol* 22, 491-506.
Chiou et al., (2002). *Starch* 54, 415-420.
Craig et al., (1998). *Plant Cell* 10, 413-426.
Denyer et al., (1996). *Plant Physiology* 112, 779-785.
Fergason. 1994. pp 55-77 in "Speciality Corns" eds, CRC Press Inc.
Filpse et al., (1996). *Planta* 198, 340.
Fisher et al., (1993). *Plant Physiol* 102:1045-1046.
Fisher et al., (1996). *Plant Physiol* 110: 611-619.
Frances et al., (1998). *Plant Mol Biol* 38, 407-415.
Fujita et al., (2003). *Plant Cell Physiol* 44, 607-618.
Fuwa et al., (1999). *Starch/Starke.* 51, 147-151.
Gao et al., (1996) *Plant Mol Biol* 30, 1223-1232.
Gao et al., (1997). *Plant Physiol* 114: 69-78.
Gao et al., (1998). *Plant Cell* 10, 399-412.
Giroux and Hannah. (1994). *Molecular and General Genetics* 243, 400-408.
Goddard et al., (1984) *Am J Clin Nutr* 39, 388-392.
Green et al., (1997). *Plant Physiology* 114, 203-212.
Hedman and Boyer, (1982). *Biochemical Genetics* 20, 483-492.
et al., (1994). *Plant J* 6, 271-282.
Hirano et al., (1998). *Mol Biol Evol* 15, 978-987.
Hirano and Sano, (2000). *Genes Genet Syst* 75, 245-249.
Isshiki et al., (1998). *Plant J* 15, 133-138.
James et al, (1995). *Plant Cell* 7, 417-429.
Jobling et al, (1999). *Plant Journal* 18, 163-171.
Juliano, B. O. (1979). in Proceedings, Workshop on Chemical Aspects of Rice Grain Quality, p. 69-90. Los Baños, Laguna, the Philippines, IRRI.
Juliano, B. O., (1985). Rice: chemistry and technology, 2nd ed. St Paul, Minn., USA, Am. Assoc. Cereal Chem. 774 pp.
Kawasaki et al., (1993). *Mol Gen Genet.* 237, 10-16.
Konik-Rose et al (2001) *Starch* 53, 14-20.
Krueger et al., (1987). *Cereal Chemistry* 64, 187-190.
Kubo et al., (1999). *Plant physiology.* 121, 399-409.
Lazo et al., (1991). *Bio/Technology* 9, 963-967.
Li et al, (1999a). *Plant physiology.* 120, 1147-1155.
Li et al., (1999b). *Theoretical and Applied Genetics* 98, 1208-1216.
Li et al., (2000). *Plant Physiology* 123, 613-624.
Li et al., (2003). *Funct Integr Genomics* 3:76-85.
Lumdubwong et al., (2000). *J Cereal Sci* 31, 63-74.
Maniatis et al., (1982). Molecular cloning: a laboratory manual. Cold Spring Harbour Laboratory Press New York.
McCreary and Helentjaris (1994). Methods in Molecular Biology, Vol. 28: Protocols for nucleic acid analysis by non-radioactive probes, 67-71, Humana Press Inc., Totawa, N.J.
Mizuno et al., (1993). *Journal of Biological Chemistry* 268, 1908419091.
Mizuno et al., (1992). *Journal of Biochemistry* 112, 643-651.
Mizuno et al., (2001). *Plant Cell Physiol* 42, 349-357.
Morell et al., (1997). *Plant Physiology* 113, 201-208.
Morell et al., (1998). *Electrophoresis* 19, 2603-2611.
Morell et al., (2003). *Plant J.* 34: 173-185.
Morrison and Laignelet (1983). *Journal of Cereal Science* 1:9-20.
Mullins et al., (1999). *European Journal of Plant Pathology* 105: 465-475.
Myers et al., (2000). *Plant Physiology* 122, 989-997.
Nakamura (2002). *Plant Cell Physiology* 43, 718-725.
Nakamura and Yamanonchi (1992). *Plant Physiol* 99: 1265-1266.
Nair et al., (1997). *Plant Sci* 122: 153-163.
Nishi et al., (2001). *Plant Physiology* 127, 459-472.
Rahman et al., (1995). *Australian Journal of Plant Physiology* 22, 793-803.
Rahman et al., (1997). *Genome* 40: 465-474.
Rahman et al., (1999). *Theor Appl Genet.* 98: 156-163.
Rahman et al., (2000). *J Cereal Sci* 31:91-110.
Rahman et al, (2001). *Plant Physiol* 123: 1314-1324.
Repellin et al., (1997). *Plant Gene Reg* 97-094
Safford et al., (1998). *Carbohydrate Polymers* 35, 155-168.
Schulman and Kammiovirta, (1991). *Starch* 43, 387-389.
Schwall et al., (2000). *Nano. Biotechnology* 18, 551-554.
Senior (1998). *Biotechnology and Genetic Engineering Reviews* 15, 79-119.
Shannon and Garwood, (1984). In *Starch: Chemistry and Technology*, Whistler et al., eds, Academic Press, Orlando, Fla., pp 25-86.
Shure et al. (1983). *Cell* 33, 225-233.
Sidebottom et al., (1998). *Journal of Cereal Science* 27, 279-287.
Smidansky et al, 2003) *Planta* 216, 656-664.
Smith et al., (2000) *Nature* 407, 319-320.
Sun et al, (1996). *Physiol Plantarum* 96, 474-483.
Sun et al., (1997). *The New Phytologist* 137, 215-215.
Sun et al, (1998). *Plant Physiol* 118, 37-49.
Takeda et al, (1986). *Carbohydr Res* 148, 299-308.
Takeda et al., (1987). *Carbohydr Res* 168, 79-88.
Takeda et al, (1993a). *Carbohydrate Research* 240, 253-262.
Takeda et al., (1993b). *Carbohydrate Research* 246, 273-281.
Terada et al, (2000). *Plant Cell Physiol* 41, 881-888.
Thomas and Atwell 1999 Starches Fagan Press, St Paul, Minn., USA pp: 13-24.
Thorbjornsen et al., (1996). *Plant Journal* 10, 243-250.
Wang et al., (1990). *Nucl Acids Res* 18, 5898.
Wang et al., (1998a). *Journal of Experimental Botany* 49, 481-502.
Wang et al, (1998b). *Acta Hort* 461, 401-407.
Wegener et al., 1994. *Mol. Gen Genet.* 245, 465-470.
Yamamori et al., (2000). *Theor. Appl. Genet.* 101, 21-29
Yamanouchi and Nakamura (1992). *Plant Cell Physiol* 33, 985-991.
Young. (1984). in Whistler et al. (eds), Academic Press, Orlando, Fla., chap 8.
Zhang et al., (1997). *Mol Biotechnol* 8, 223-231.
Zikiryaeva and Kasimov, (1972). *Uzbekskii Biologicheskii Zhurnal* 6, 18-20.
Zwar and Chandler, (1995). *Planta* 197, 39-48.

The invention claimed is:

1. Rice starch granules, comprising (i) starch, (ii) a reduced level of starch branching enzyme IIa (SBEIIa) protein, (iii) a reduced level of starch branching enzyme IIb (SBEIIb) protein, and (iv) a reduced level of starch branching enzyme I (SBEI) protein, the reduced level of SBEIIa protein, of SBEIIb protein, and of SBEI protein being relative to rice starch granules of an Indica variety, wherein the proportion of amylose in the starch of the starch granules is at least 40% (w/w) as measured by an iodometric method.

2. The rice starch granules of claim 1, wherein the proportion of amylose in the starch of the rice starch granules is at least 60% (w/w).

3. The rice starch granules of claim 1, wherein the starch in the rice starch granules has an increased gelatinization temperature relative to starch in rice starch granules of the Indica variety.

4. The rice starch granules of claim 1, wherein the starch in the rice starch granules comprises an elevated level of resistant starch relative to the starch in rice starch granules of the Indica variety.

5. The rice starch granules of claim 1, wherein the starch in the rice starch granules comprises an increased amount of dietary fibre relative to the starch in rice starch granules of the Indica variety.

6. A product comprising rice starch granules, comprising (i) starch, (ii) a reduced level of starch branching enzyme IIa (SBEIIa) protein, (iii) a reduced level of starch branching enzyme IIb (SBEIIb) protein, and (iii)(iv) a reduced level of starch branching enzyme I (SBEI) protein, the reduced level of SBEIIa protein, of SBEIIb protein, and of SBEI protein being relative to rice starch granules of an Indica variety, wherein the proportion of amylose in the starch of the starch granules is at least 40% (w/w) as measured by an iodometric method.

7. The product of claim 6, wherein the proportion of amylose in the starch of the rice starch granules of the product is at least 60% (w/w).

8. The product of claim 6, which is a food product.

9. The food product of claim 8, which has a reduced Glycaemic Index (GI).

10. A process for producing a rice plant having a reduced level of starch branching enzyme IIa (SBEIIa), starch branching enzyme IIb (SBEIIb), and starch branching enzyme I (SBEI) proteins and/or enzyme activities in the endosperm which comprises:

a) mutagenising a seed having a reduced level of SBEIIa and SBEIIb protein and/or enzyme activity to also have a reduced level of SBEI protein and/or enzyme activity; or
crossing a plant having a reduced level of SBEIIa and SBEIIb protein and/or enzyme activity with a plant having a reduced level of SBEI protein and/or enzyme activity; and
b) identifying a rice plant having reduced level of each of SBEIIa, SBEIIb, and SBEI proteins and/or enzyme activities in the endosperm.

11. The process of claim 10, wherein the rice plant identified in step b) comprises a genetic variation selected from the group consisting of
(i) a mutation of an SBEIIa gene which inhibits SBEIIa expression and/or activity, and
(ii) an introduced nucleic acid which inhibits SBEIIa expression and/or activity,
and
a genetic variation selected from the group consisting of
(i) a mutation of an SBEIIb gene which inhibits SBEIIb expression and/or activity, and
(ii) an introduced nucleic acid which inhibits SBEIIb expression and/or activity,
and
a genetic variation selected from the group consisting of
(i) a mutation of an SBEI gene which inhibits SBEI expression and/or activity, and
(ii) an introduced nucleic acid which inhibits SBEI expression and/or activity.

12. The process of claim 11, wherein the rice plant identified in step b) comprises
(i) a mutation of an SBEIIa gene which inhibits SBEIIa expression and/or activity,
(ii) a mutation of an SBEIIb gene which inhibits SBEIIb expression and/or activity, and
(iii) a mutation of an SBEI gene which inhibits SBEI expression and/or activity.

13. The process of claim 11, wherein the rice plant identified in step b) comprises
(i) a mutation of an SBEIIa gene which inhibits SBEIIa expression and/or activity,
(ii) a mutation of an SBEIIb gene which inhibits SBEIIb expression and/or activity, and
(iii) CO introduced nucleic acid which inhibits SBEI expression and/or activity.

* * * * *